(12) United States Patent
Li et al.

(10) Patent No.: US 10,398,547 B2
(45) Date of Patent: Sep. 3, 2019

(54) IMPLANT WITH ANCHORING DEVICE FOR HEART VALVE DISEASE

(71) Applicant: NINGBO JENSCARE BIOTECHNOLOGY CO., LTD., Ningbo (CN)

(72) Inventors: Jianan Li, Ningbo (CN); Shiwen Lv, Ningbo (CN); Zhiyun Xu, Ningbo (CN); Yibin Li, Ningbo (CN); Zhi Chen, Ningbo (CN)

(73) Assignee: NINGBO JENSCARE BIOTECHNOLOGY CO., LTD. (CN)

( * ) Notice: Subject to any disclaimer, the term of this patent is extended or adjusted under 35 U.S.C. 154(b) by 218 days.

(21) Appl. No.: 15/398,878

(22) Filed: Jan. 5, 2017

(65) Prior Publication Data
US 2017/0112622 A1    Apr. 27, 2017

Related U.S. Application Data

(63) Continuation of application No. PCT/CN2015/080203, filed on May 29, 2015.

(30) Foreign Application Priority Data

Jul. 7, 2014 (CN) .......................... 2014 1 0317001

(51) Int. Cl.
*A61F 2/24* (2006.01)
*A61B 17/064* (2006.01)
(Continued)

(52) U.S. Cl.
CPC .......... *A61F 2/2418* (2013.01); *A61B 17/068* (2013.01); *A61B 17/0644* (2013.01);
(Continued)

(58) Field of Classification Search
CPC .............. A61B 17/064; A61B 17/0644; A61B 17/0645; A61B 17/068; A61F 2/24;
(Continued)

(56) References Cited

U.S. PATENT DOCUMENTS 8,579,964 B2    11/2013  Lane et al.
2005/0107811 A1  5/2005  Starksen et al.
(Continued)

FOREIGN PATENT DOCUMENTS

CN    201949181 U    8/2011
CN    103079498 A    5/2013
(Continued)

OTHER PUBLICATIONS

PCT International Search Report dated Aug. 14, 2015 from corresponding Application No. PCT/CN2015/080203, 9 pages.

*Primary Examiner* — Todd J Scherbel
(74) *Attorney, Agent, or Firm* — Dilworth IP, LLC

(57) ABSTRACT

An implant with anchoring device for heart valve disease comprises a cardiac valve prosthesis (1), at least two sets of anchoring needles (2) and at least two sets of anchoring needle releasing devices (3). Proximal end of the anchoring needles (2) are provided with anti-disengagement ends (23). The anchoring needle releasing devices (3) are detachably connected to the cardiac valve prosthesis (1). The anchoring needle releasing devices (3) comprise delivery tubes (31) and shafts (32). Distal sections of the anchoring needle releasing devices (3) are in preset shapes. The shafts (32) can be pushed to force the anchoring needles (2) to move toward the distal ends of the delivery tubes (31), so that the cardiac valve prosthesis (1) is fixed between autogenous tissue (6) and the anti-disengagement ends (23) to achieve accurate positioning and firm anchoring of the cardiac valve prosthesis (1).

13 Claims, 20 Drawing Sheets

(51) Int. Cl.
 *A61B 17/068* (2006.01)
 *A61F 2/966* (2013.01)
 *A61B 17/00* (2006.01)
(52) U.S. Cl.
 CPC .......... *A61F 2/2436* (2013.01); *A61F 2/966* (2013.01); *A61B 2017/00309* (2013.01); *A61B 2017/00867* (2013.01); *A61B 2017/0645* (2013.01); *A61B 2017/0649* (2013.01); *A61F 2220/0016* (2013.01); *A61F 2230/0006* (2013.01); *A61F 2230/0065* (2013.01)
(58) Field of Classification Search
 CPC ........ A61F 2/2427; A61F 2/2436; A61F 2/95; A61F 2/962; A61F 2/966; A61F 2002/9665
 See application file for complete search history.

(56) References Cited

U.S. PATENT DOCUMENTS

| | | |
|---|---|---|
| 2008/0058868 A1 | 3/2008 | To et al. |
| 2008/0306586 A1* | 12/2008 | Cartledge ........ A61B 17/00234 623/2.11 |
| 2010/0280606 A1 | 4/2010 | Naor |
| 2014/0107758 A1 | 4/2014 | Glazier |

FOREIGN PATENT DOCUMENTS

| | | |
|---|---|---|
| CN | 104055600 A | 9/2014 |
| CN | 104055601 A | 9/2014 |
| CN | 104055602 A | 9/2014 |
| CN | 104055603 A | 9/2014 |
| CN | 104055604 A | 9/2014 |

* cited by examiner

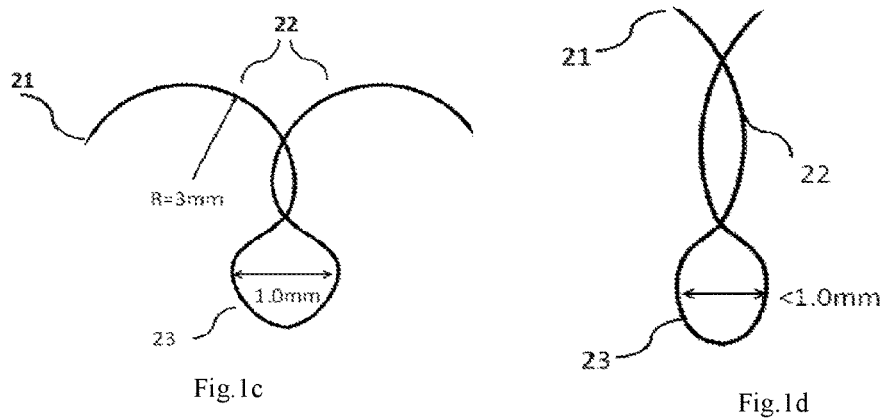
Fig.1c
Fig.1d
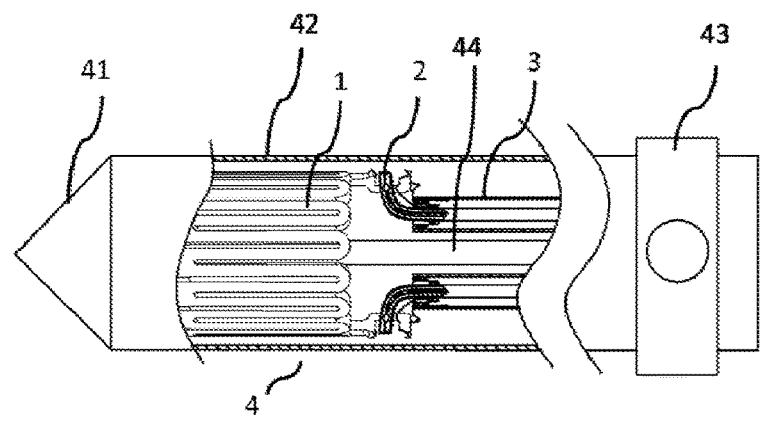
Fig.2a
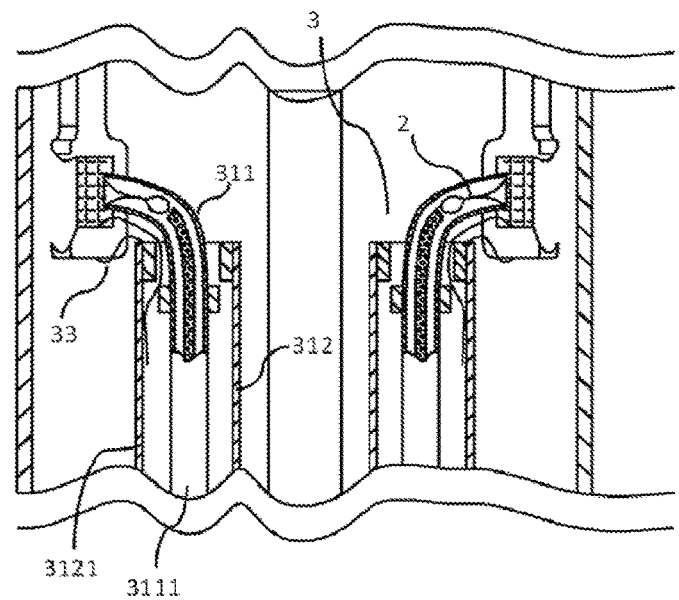
Fig.2b

A—A

B — B

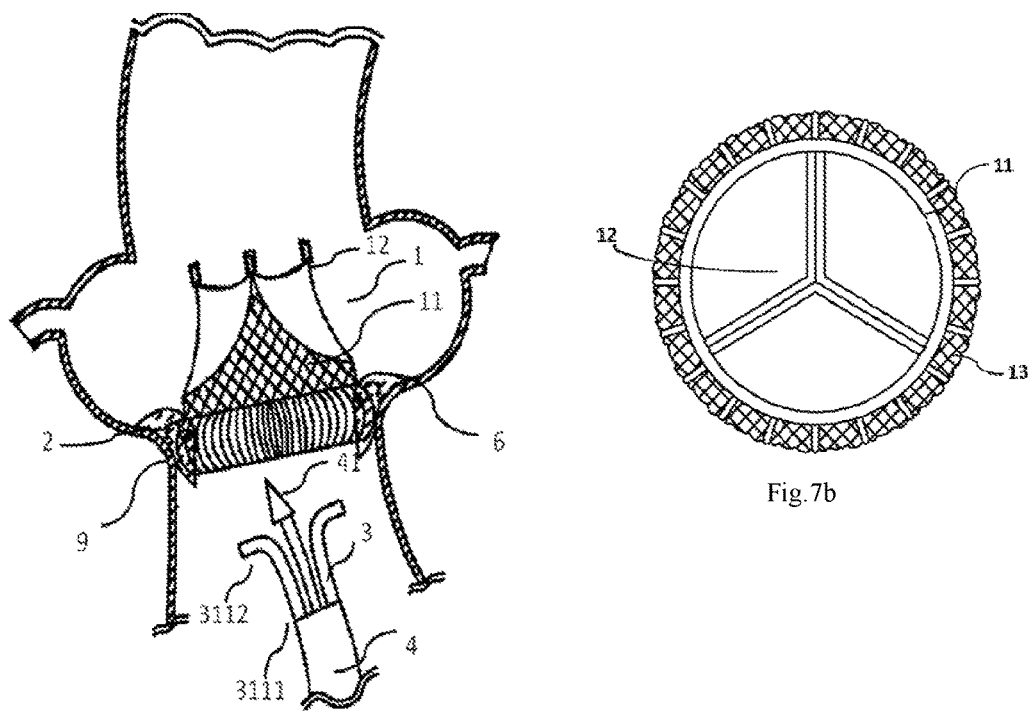
Fig.7a
Fig.7b
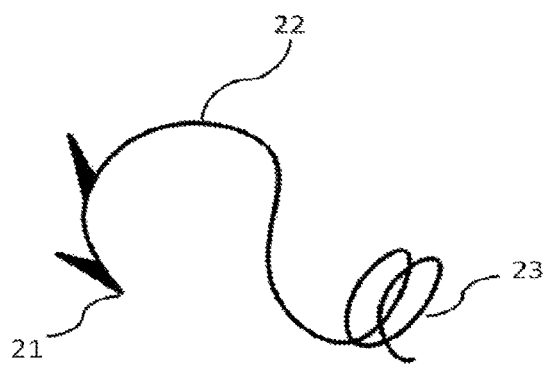
Fig.7c

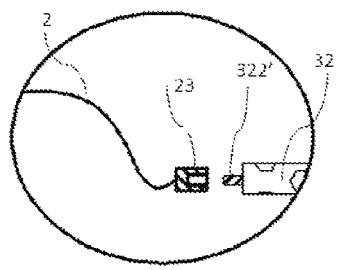
Fig.8k
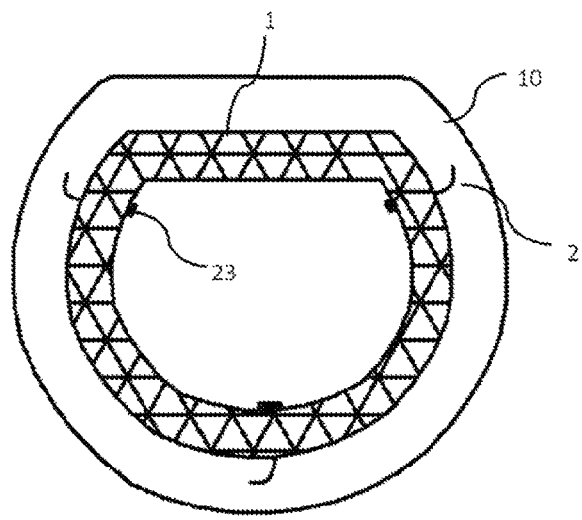
Fig.8l
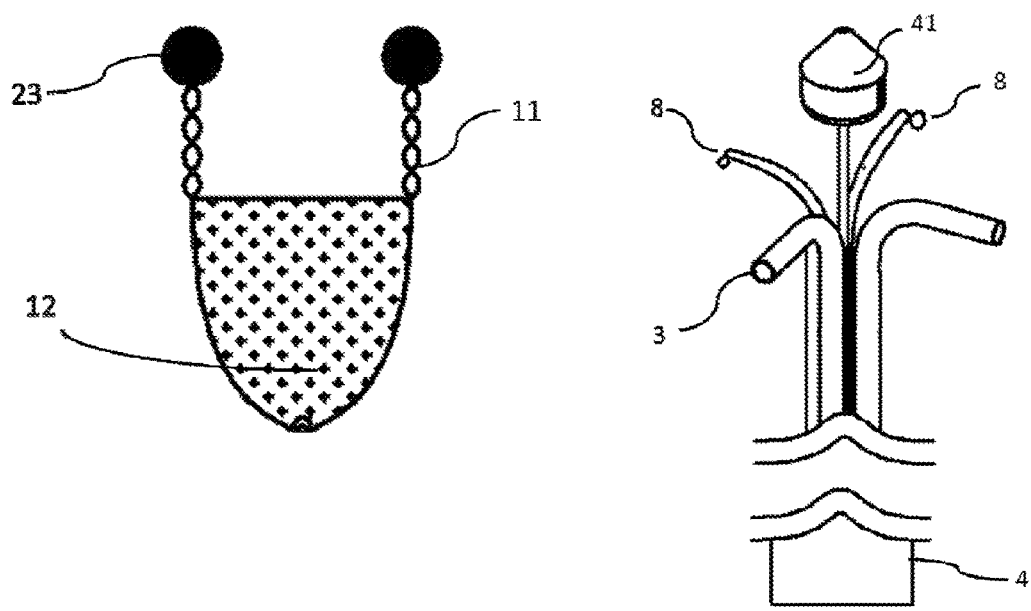
Fig.9a
Fig.9b

IMPLANT WITH ANCHORING DEVICE FOR HEART VALVE DISEASE

CROSS REFERENCE TO RELATED APPLICATIONS

This application is a continuation application of PCT Patent Application No. PCT/CN2015/080203, entitled "Implant with Anchoring Device for Heart Valve Disease", filed on May 29, 2015, which claims priority to Chinese Patent Application No. 201410317001.9, entitled "Implant with Anchoring Device for Heart Valve Disease", filed on Jul. 7, 2014, the entire contents of which are incorporated herein by reference.

TECHNICAL FIELD

The present disclosure relates to the field of medical equipment, and more particularly, to an implant with anchoring device for heart valve disease.

BACKGROUND

The cardiac valve mainly refers to the left atrioventricular valve, the right atrioventricular valve, the pulmonary valve and the aortic valve. The tricuspid valve of the right atrioventricular orifice comprises three triangular-like cusps or segments, and their bases are attached to a fibrous ring surrounding the atrioventricular orifice; the fibrous ring, the valve, the chordae tendineae and the papillary muscle are regarded functionally as a tricuspid valvar complex. The fibrous ring of the left atrioventricular orifice, the mitral valve, the chordae tendineae and the papillary muscles are an integral entirety functionally and structurally, and are referred to as a mitral valve complex. The aorta is located at the center of the fibrous skeleton of the heart. Three semilunar aortic valves leaflets are attached on the tissue ring constructed by dense connective tissues. The pulmonary valve is located at the left front of the aortic valve, and the pulmonary valve annulus is attached on the trunk of the pulmonary valve; commonly, there are three connected valve annulus, that is, the front curved valve annulus, left curved valve annulus and right curved valve annulus. During the life of a human being, the natural cardiac valve can repeatedly open and close for more than 2700 million times.

AS (Aortic Stenosis) or PS (Pulmonary Stenosis) is one of the common valvular diseases. For a long time, aortic valve replacement is known as the only long-term and effective treatment. Thanks to continuous innovations of cardiac intervention methods and medical devices, PAVR (Percutaneous Aortic Valve Replacement,) has gradually become the mainstream of surgery. How to accurately and firmly position the implant is one of the key factors for a successful surgery.

However, function insufficiency of the mitral valve and tricuspid valve is one of the most common heart diseases, such as the tricuspid valve insufficiency caused by high pressure of pulmonary artery and physiological expansion of the tricuspid valve, the mitral valve insufficiency or the tricuspid valve insufficiency caused by diseases accompanied by prolapse of the mitral valve or prolapse of the tricuspid valve, and tricuspid stenosis or mitral stenosis caused by valve damages resulted from rheumatic inflammation.

Among patients with mitral valve insufficiency, there are about 2 million to 2.5 million people in the United States suffering from mitral regurgitation, and it is expected that the number of the patients will rise up to 4.8 million in 2030, and the incidence rate of the disease in China is about 0.5% to 2%. In the United States and other western developed countries, the mitral valve insufficiency is mainly caused by mucinous degenerative diseases, which accounts for about 45% to 65%. In many developing countries, rheumatic lesion is the main reason of mitral valve diseases, which accounts for about 80% (Zhang Baoren, Xu Zhiyun, chief editors, *Cardiac Valve Surgery* [M], People's Medical Publishing House, 2007, 478-488). Mitral regurgitation can be divided into three types, that is, functional, degenerative or mixed mitral regurgitation. Functional mitral regurgitation and degenerative mitral regurgitation are most common Functional mitral regurgitation is usually secondary to impaired motion function of the left ventricular wall, left ventricular expansion or function disorder of the papillary muscles, and is common among patients with heart failure. Some of the patients suffer from ischemic mitral regurgitation secondary to coronary heart disease or suffer from mitral regurgitation related with nonischemic cardiomyopathy. The degenerative mitral regurgitation is commonly regarded as pathological changes of valve structure or pathological changes of subvalvular structure, which comprises the abnormal extension or fracture of the chordae tendineae.

Traditional therapy of cardiac valve disease includes drug therapy for mild illness and surgery methods for illness with corresponding surgery indications. Among which, the typical thoracotomy and open heart surgery are too invasive, which need to establish an extracorporeal circulation, and have higher incidence of complications and risk of infection. In order to reduce the risk of surgery, Percutaneous Annuloplasty, Percutaneous Valve Replacement, and Percutaneous valve Repair are developed. In all of these methods, there exist problems that the positioning between the cardiac valve implant and the autogenous tissue is inaccurate and the anchoring is not firm.

In order to solve the problems above, Chinese patent No. CN201120022195.1 provides an ascending aorta endovascular exclusion stent with a filled type fixing capsule. The filled type fixing capsule is stitched or adhered to the outer side of the coated cylindrical stent. The capsule is filled with water absorptive material, which is water-swellable in the blood vessel, thereby fixing the stent and preventing displacement. However, according to this patent, the tube diameter of the delivery sheath is limited by the fixing capsule.

The U.S. patent application with pub. No. US2010280606A1 describes a valve prosthesis adapted to operate in conjunction with native heart valve leaflets. The valve prosthesis comprises a frame, and the frame is hollow. The anchor portion can slide in the hollow frame under the push of the delivery system so as to pierce the tissue. The diameter of the tail section of the anchor portion is greater than the internal diameter of the hollow frame, which can perform the function of fixing the frame and the tissue. However, the anchor portion, whether it is released or not, is one part of the valve prosthesis, and, when the anchor portion is pushed, it will be limited due to the shape of the frame and limited by the forces exerted by the frame.

The U.S. Pat. No. 8,579,964B2 and the Chinese patent No. CN103079498A disclose a method of anchoring a prosthetic valve in a patient's heart. Said method comprising: providing the prosthetic valve, wherein the prosthetic valve comprises an anchor having an atrial skirt, an annular region, a ventricular skirt, and a plurality of valve leaflets, wherein the anchor has a collapsed configuration for delivery to the heart and an expanded configuration for anchoring with the heart. The anchor disclosed by the patents comprises anchoring tabs which are combined with the implanted prosthesis, and the anchor can be provided with barbs. However, according to the anchoring method of the patents, the atrial skirt and the ventricular skirt will damage the structures of the patient's annulus and valve themselves, so the method is only applicable to valve replacement.

The U.S. patent applications No. US2005107811A1 and No. US2008058868A1 disclose an anchoring system and a delivery method thereof, wherein the anchor is made of shape memory alloy, and the anchor has two curved legs that cross in a single turning direction to form a loop. The anchor can assume different configurations such as a deployed configuration and a delivery configuration, and the anchor may switch between these two different configurations. In operation, the anchor may be released from a delivery configuration so that the shape memory alloy self-expands into the deployed configuration, so that the two legs of the anchor may penetrate the tissue in a curved pathway to fix the tissue. According to the anchoring system and the delivery method thereof, the legs of the anchor penetrate the tissue only under the forces of the shape memory alloy during its deployment, for some penetrating positions such as those in the tough tissue, for example, in the endocardium, the piercing forces may not be large enough, as a result, the anchor easily falls off in the process of piercing, and after it is pierced into the tissue, the anchor is not fixed stably and easily falls off.

The current clinical findings show that the techniques described above can take some effects on anchoring and on interventional therapy for valvular heart diseases, but there is still not a satisfactory implant with anchoring device for heart valve disease in the prior art, which can realize accurate positioning and firm anchoring of the functional cardiac valve prosthesis at the position where the therapy is required.

SUMMARY

The present disclosure aims to overcome the limitation of the prior art and to provide an implant with anchoring device for heart valve disease. The implant with anchoring device for heart valve disease of the present disclosure can realize the accurate positioning and firm anchoring, shorten the operation time greatly, minimize the surgical trauma and increase the cure rate.

An objective of the present invention is realized by the following technical scheme:

An implant with anchoring device for heart valve disease comprises a cardiac valve prosthesis, at least two sets of anchoring needles, and at least two sets of anchoring needle releasing devices; a most distal end of the anchoring needle is sharp; a distal section of the anchoring needle has a preset shape; a proximal end of the anchoring needle is provided with an anti-disengagement end; the anchoring needle releasing device is detachably connected to the cardiac valve prosthesis; the anchoring needle releasing device comprises a delivery tube and a shaft; a distal section of the anchoring needle releasing device is in a preset shape, so as to enable the distal section of the delivery tube bend wholly or partially, and to enable the distal end of the delivery tube presses tightly against the cardiac valve prosthesis or presses tightly against autogenous tissue before the anchoring needle is moved; the most distal end of the delivery tube has a rigid section; a bendable part of the delivery tube is a bent section; a length d from the most distal end of the delivery tube to the most proximal end of the bent section is larger than 1/6 of circumference of a circle formed by the minimum radius of a native heart valve annulus of a patient; the anchoring needle is pre-placed inside the distal section of the delivery tube in a stretched state; the shaft is arranged inside the delivery tube; the anchoring needle is disposed beside a distal end of the shaft; the shaft can be pushed to force the anchoring needles to move toward the distal end of the delivery tube; the distal section of the anchoring needle can restore to the preset shape after the anchoring needle is pushed out of the delivery tube; and the cardiac valve prosthesis is fixed between autogenous tissue and the anti-disengagement end of the anchoring needle.

Objectives of the present invention are realized further by the following technical schemes: In some of the embodiments, a length of the rigid section of the delivery tube is greater than, or equals to one tenth of a full length of the anchoring needle. Preferably, the length of the rigid section of the delivery tube is greater than, or equals to half of the full length of the anchoring needle; preferably, the length of the rigid section of the delivery tube is greater than, or equals to the full length of the anchoring needle.

In some of the embodiments, the distal section of the delivery tube is pre-shaped, which enables the distal section of the shaft to bend along with the pre-shaped distal section of the delivery tube.

In some of the embodiments, the distal section of the shaft is pre-shaped, which enables the bendable part of the delivery tube to bend along with the pre-shaped distal section of the shaft.

In some of the embodiments, both the distal section of the delivery tube and the distal section of the shaft are pre-shaped, which enables the distal section of the delivery tube and the distal section of the shaft to bend together.

In some of the embodiments, the implant with anchoring device for heart valve disease further comprises a supporting device and an operating member for the supporting device; the operating member for the supporting device is fixedly connected to a proximal end of the supporting device; a distal section of the supporting device is bendable, which makes the distal section of the supporting device press against the autogenous tissue when the supporting device is released.

In some of the embodiments, the implant with anchoring device for heart valve disease further comprises a supporting device and a delivery system; the delivery system comprises a tip, an outer sheath tube, a sheath core, and an operating member; the sheath core is arranged inside the outer sheath tube; a distal end of the sheath core is fixedly connected to the tip; a proximal end of the sheath core is fixedly connected to the operating member; the cardiac valve prosthesis, the anchoring needle releasing device, and the supporting device are arranged between the outer sheath tube and the sheath core; a proximal end of the supporting device is fixedly connected to the operating member of the delivery system; or the distal section of the supporting device is fixedly connected to the tip of the delivery system; or the proximal end of the supporting device is fixedly connected to the operating member of the delivery system, and the distal section of the supporting device is fixedly connected to the tip of the delivery system; and when the anchoring needle releasing device is released, the supporting device exerts a supporting force on the anchoring needle releasing device, the supporting force can resist the acting force exerted on the anchoring needle releasing device by the autogenous tissue, thereby enhancing the success rate of piercing.

In some of the embodiments, the supporting device is made of stainless steel tubes; the proximal end of the supporting device is fixedly connected to the operating member of the delivery system; the distal section of the supporting device has slits, which enables the distal section of the supporting device to bend; the distal section of the supporting device is movably connected to a rigid supporting rod; and a distal end of the supporting rod is movably connected to the tip.

In some of the embodiments, the delivery tube is detachably connected to the cardiac valve prosthesis through a connecting wire.

In some of the embodiments, the delivery tube comprises at least two layers of tubes; one layer tube is disposed inside another layer tube; one end of the connecting wire is fixed at a distal section of either of the layer tube; another end of the connecting wire goes through the cardiac valve prosthesis and is winded back and clamped between distal sections of adjacent two layers of tubes; an operating member of the delivery tube is fixedly connected to a proximal end of the delivery tube; the at least two layers of tubes can be moved to detach a detachable connection between the delivery tube and the cardiac valve prosthesis by operating the operating member of the delivery tube; the implant with anchoring device for heart valve disease further comprises a delivery system; the delivery system comprises a tip, an outer sheath tube, a sheath core, and an operating member; the sheath core is arranged inside the outer sheath tube; a distal end of the sheath core is fixedly connected to the tip; the proximal end of the sheath core is fixedly connected to the operating member; the cardiac valve prosthesis and the anchoring needle releasing device are arranged between the outer sheath tube and the sheath core; a proximal end of the delivery tube is fixedly connected to the operating member; a detachable connection between the delivery tube and the cardiac valve prosthesis can be detached by operating the operating member.

In some of the embodiments, the connecting wire is made of a single strand or a plurality of strands of nickel-titanium alloy wires or stainless steel wires; or the connecting wire is made of a single strand or a plurality of strands of polymer bars or polymer wires.

In some of the embodiments, a distal section of the delivery tube is fixedly connected to controlling wire to make it bend; a proximal end of the controlling wire is fixedly connected to an operating member for bend adjusting.

In some of the embodiments, the anti-disengagement end of the anchoring needle is formed by further extending and winding the proximal end of the anchoring needle.

In some of the embodiments, the shaft is detachably connected to the anti-disengagement end of the anchoring needle.

In some of the embodiments, the anchoring needle is fixedly connected on the cardiac valve prosthesis; and a detachable connection between the anchoring needle releasing devices and the cardiac valve prosthesis is realized by a detachable connection between the anchoring needle and the anchoring needle releasing devices. In some of the embodiments, the anti-disengagement end of the anchoring needle is fixedly connected to the shaft.

In some of the embodiments, the distal section of the anchoring needle has a preset shape selected from one or a combination of the following shapes: a spiral, a circle, an arc, a combination of an arc line and a straight line, a bifurcated double hook, a 3D-curved form, and a multi-segment curved form. The distal end of the anchoring needle has no barbs, has a barb, or has a plurality of barbs.

In some of the embodiments, the cardiac valve prosthesis is a replacement prosthesis or a device for preventing cardiac valve regurgitation. The cardiac valve prosthesis is made of one or a combination of metallic materials, animal tissues and polymers.

As compared with the prior art, the present disclosure has the following advantages:

1. The shaft in the present invention is configured to control the movement of the anchoring needle. When the shaft is pushed, the thrust, in combination with one or a combination of the supporting force of the cardiac valve prosthesis, the acting force of the delivery tube or the supporting device in some of the embodiments, and the constraint force of the tube wall of the rigid section of the distal section of the delivery tube exerted on the anchoring needle, enables anchoring needles with various preset shapes to be pushed into the tough endocardium and cardiac tissue, so as to make up the defects in the prior art that the piercing force of the anchoring needle is not large enough to pierce the endocardium and cardiac tissue successfully. The present invention solves the problems that the anchoring needle is not easy to position and easily falls off in the process of the piercing, and the problems that the anchoring needle is not fixed firmly and easily slips off under the washing of the blood after it is pierced into the tissues. The technical schemes of the present disclosure sufficiently realize the functions of accurate positioning and firm anchoring.

2. The distal section of the delivery tube can bend wholly or partially, so that the distal end of the delivery tube can bend and press perpendicularly against the tough targeting piercing position. What's more, the distal section of the delivery tube is a rigid section, so that the distal end of the delivery tube can press against the autogenous tissue tightly, thereby ensuring the angle and the path of the needle while it is pushed out, and enabling anchoring needles with various preset shapes to be pushed into the tough and soft tissue.

3. The anchoring needle releasing device of the present invention is detachably connected to the cardiac valve prosthesis, which not only ensures the accurate positioning and releasing of the cardiac valve prosthesis, but also ensures that, after the implanted device is positioned, released and implanted, all the non-implanted devices can be retracted from the human body, and the additional implanted material is less.

4. The length of the rigid section of the present invention is limited, which not only ensures that the sharp most distal end of the anchoring needle can be confined in the delivery tube, but also decreases the affects of the rigid section on the bending performance of the delivery tube.

5. The distal section of the anchoring needle is limited to have a preset shape and size, which prevents the anchoring needle from damaging the conduction bundle and the coronary artery while and after it is pushed into tissue, and decreases the probability to install a pacemaker for a patient after operation. What's more, the proximal end of the anchoring needle is provided with the anti-disengagement end, which limits the displacement of the cardiac valve prosthesis and the anchoring needle relative to the piercing position after the anchoring needle is moved in place, thereby realizing fixation.

6. The technology of the present disclosure is also applicable to the replacement, reconstruction, or repair therapy for the aortic valve, the pulmonary valve, the tricuspid valve, or the mitral valve, especially for those surgeries through the cardiac apex approach or through the heart atrium approach.

BRIEF DESCRIPTION OF DRAWINGS

FIGS. 1a-1d are structural schematic diagrams illustrating the implant with anchoring device for heart valve disease, which is applicable to the mitral valve replacement surgery through the cardiac apex approach to the heart, wherein, FIG. 1a is a schematic diagram where the cardiac valve prosthesis and the anchoring needle are released and the positing and fixing operations are completed; FIG. 1b is a structural schematic diagram of the cardiac valve prosthesis; FIG. 1c is a structural schematic diagram of the anchoring needle; FIG. 1d is a schematic diagram illustrating the state of the anchoring needle when it is pre-placed in the distal section of the delivery tube;

FIGS. 2a-2g are schematic diagrams illustrating the operating process of the implant with anchoring device for heart valve disease of the present invention; wherein, FIG. 2a is a schematic diagram illustrating the cardiac valve prosthesis, the anchoring needle and the anchoring needle releasing device, which are pressed and held radially inside the sheath tube; FIG. 2b is an enlarged partial view of the anchoring needle releasing device in FIG. 2a; FIG. 2c is an enlarged partial view of the delivery tube; FIGS. 2d-2g are schematic diagrams illustrating the process of releasing the anchoring needle so as to complete the detachable connection between the delivery tube and the cardiac valve prosthesis;

FIGS. 3a-3e are structural schematic diagrams illustrating the implant with anchoring device for heart valve disease, which is applicable to the tricuspid valve replacement surgery through the cardiac apex approach to the heart, wherein, FIG. 3a is a schematic diagram illustrating the process of releasing the cardiac valve prosthesis and the anchoring needle so as to finish the positing and fixing operations; FIG. 3b is a structural schematic diagram of the releasing device; FIG. 3c is a structural schematic diagram of the cardiac valve prosthesis; FIG. 3d is a structural schematic diagram of the anchoring needle; FIG. 3e is a schematic diagram illustrating the extended state of the anti-disengagement end of the anchoring needle which is pre-placed in the delivery tube;

FIGS. 4a-4f are schematic diagrams illustrating the process of releasing the anchoring needle so as to complete the detachable connection between the delivery tube and the cardiac valve prosthesis, wherein, FIG. 4f is a structural schematic diagram illustrating the cardiac valve prosthesis which is fixed on the autogenous tissue by four anchoring needles;

FIGS. 5a-5g are structural schematic diagrams illustrating the implant with anchoring device for heart valve disease, which is applicable to the mitral valve repair surgery through the cardiac apex approach to the heart, wherein, FIG. 5a is a schematic diagram illustrating the process of releasing the cardiac valve prosthesis and the anchoring needle so as to complete the positing and fixing operations; FIG. 5b is a structural schematic diagram of the releasing device; FIG. 5c is a structural schematic diagram of the cardiac valve prosthesis; FIG. 5d is a structural schematic diagram of the anchoring needle; FIGS. 5e-5g are schematic diagrams illustrating partial structure of the delivery tube;

FIGS. 6a-6e are schematic diagrams illustrating the process of releasing the anchoring needle so as to complete the detachable connection between the delivery tube and the cardiac valve prosthesis, wherein, FIG. 6e is a structural schematic diagram illustrating the cardiac valve prosthesis which is fixed on the autogenous tissue by three anchoring needles; FIGS. 6f-6k are structural schematic diagrams illustrating the embodiments of the supporting device, wherein, FIG. 6g is a sectional view taken along lines A-A, illustrating the supporting device in the outer sheath tube in the embodiment shown in FIG. 6f; FIG. 6i is a sectional view taken along lines B-B, illustrating the supporting device in the outer sheath tube in the embodiment shown in FIG. 6h; FIG. 6k is a structural schematic diagram taken from a different angle of FIG. 6j;

FIGS. 7a-7i are structural schematic diagrams illustrating the implant with anchoring device for heart valve disease, which is applicable to the aortic valve replacement surgery through the cardiac apex approach to the heart, and illustrating partial process of operating the instrument, wherein: FIG. 7a is a schematic diagram illustrating the process of releasing the cardiac valve prosthesis and the anchoring needle so as to complete the positing and fixing operations; FIG. 7b is a structural schematic diagram of the cardiac valve prosthesis; FIG. 7c is a structural schematic diagram of the anchoring needle; FIGS. 7d-7i are schematic diagrams illustrating the process of releasing the anchoring needle so as to complete the detachable connection between the delivery tube and the cardiac valve prosthesis, wherein, FIG. 7h is an enlarged partial view of FIG. 7g; FIG. 7i is a structural schematic diagram illustrating the cardiac valve prosthesis which is fixed nearby the aortic valve annulus by two anchoring needles;

FIGS. 8a-8l are structural schematic diagrams illustrating the implant with anchoring device for heart valve disease, which is applicable to mitral valve reconstruction surgery through the heart atrium approach to the heart, and illustrating partial process of operating the instrument, wherein, FIG. 8a is a schematic diagram illustrating the process of releasing the cardiac valve prosthesis and the anchoring needle so as to complete the positing and fixing operations; FIGS. 8b-8c are structural schematic diagrams of the anchoring needle releasing device; FIG. 8d is a structural schematic diagram of the anchoring needle; FIGS. 8e-8k are schematic diagrams illustrating the process of releasing the anchoring needle so as to complete the detachable connection between the delivery tube and the cardiac valve prosthesis; wherein, FIG. 8f is an enlarged partial view of FIG. 8e; FIG. 8k is an enlarged partial view of FIG. 8j; FIG. 8l is a structural schematic diagram illustrating the cardiac valve prosthesis which is fixed on the mitral valve annulus by three anchoring needles;

FIGS. 9a-9h are structural schematic diagrams illustrating the implant with anchoring device for heart valve disease, which is applicable to the mitral valve or tricuspid valve repair surgery through the cardiac apex approach to the heart, and illustrating partial process of operating the instrument, wherein, FIG. 9a is a structural schematic diagram of the cardiac valve prosthesis, which has fixedly connected anchoring needles; FIG. 9b is a structural schematic diagram of the anchoring needle releasing device; FIGS. 9c-9h are schematic diagrams illustrating the process of releasing the anchoring needle so as to complete the detachable connection between the anchoring needle releasing device and the cardiac valve prosthesis.

DETAILED DESCRIPTION OF DISCLOSED EMBODIMENTS

In order to make the objectives, technical schemes and advantages of the present disclosure more apparent and better understood, the present disclosure will be described in more details with reference to the accompanying figures and embodiments.

The proximal end as described in the present disclosure refers to the end nearer to the operating member of the delivery system or proximal to the surgical operator, and the distal end refers to the end farther from the operating member of the delivery system or farther from the surgical operator.

The First Embodiment

Figure 1A:
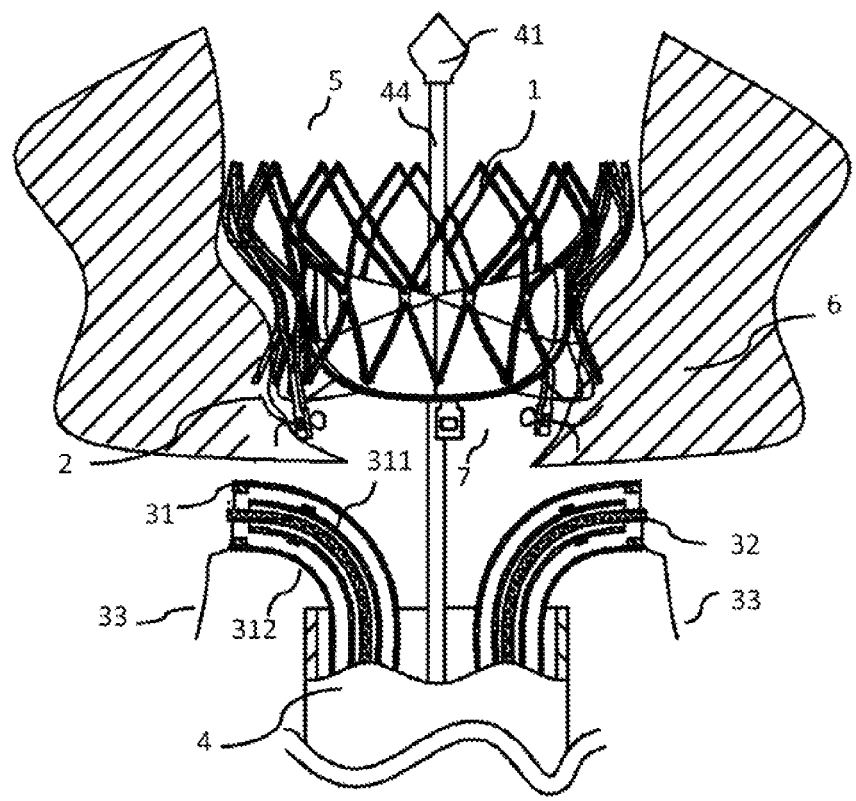
Figure 1B:
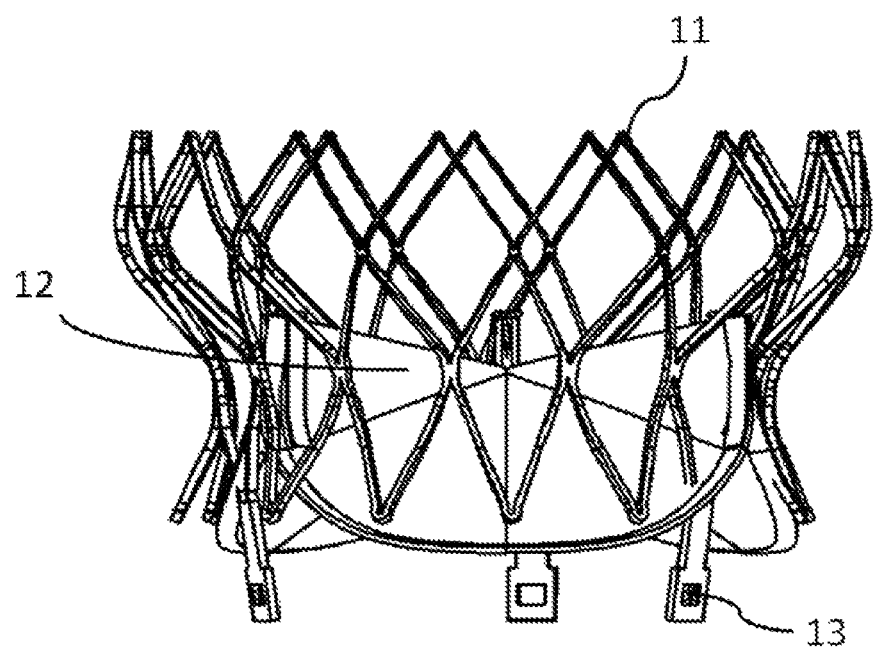
Figure 2C:
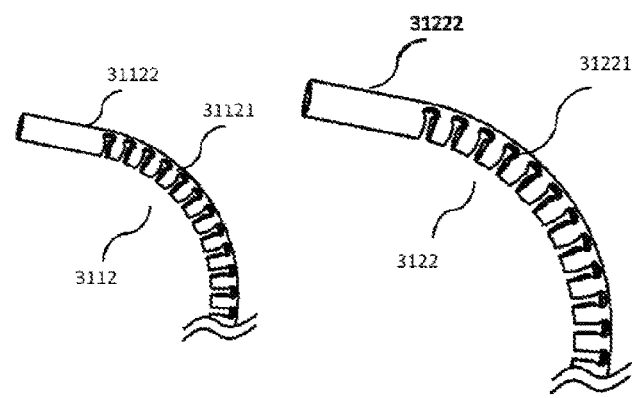
Figure 2D:
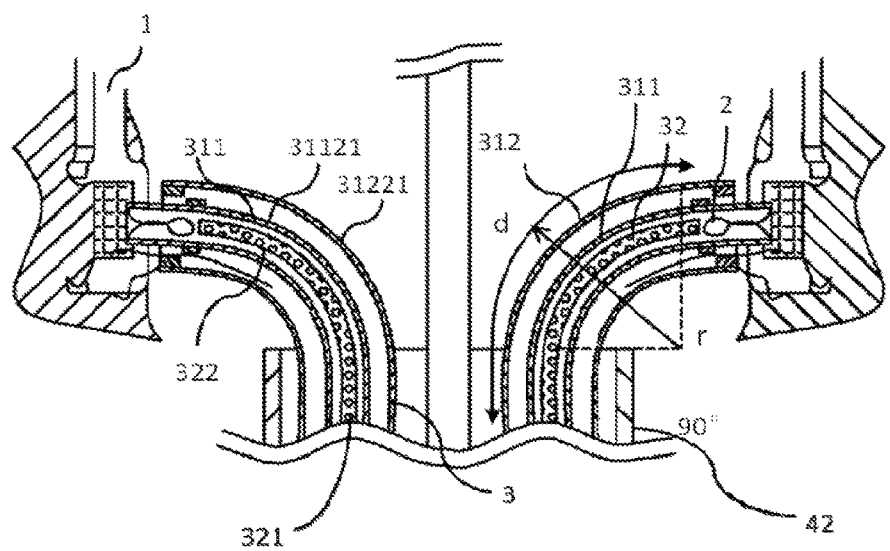
Figure 2E:
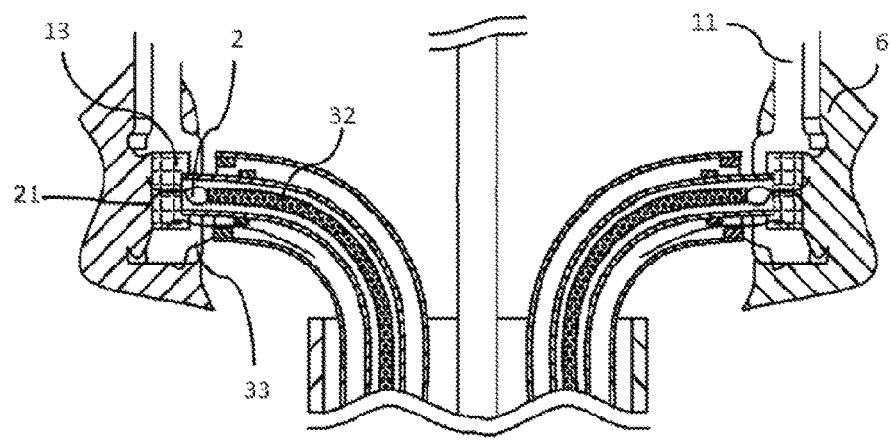
Figure 2F:
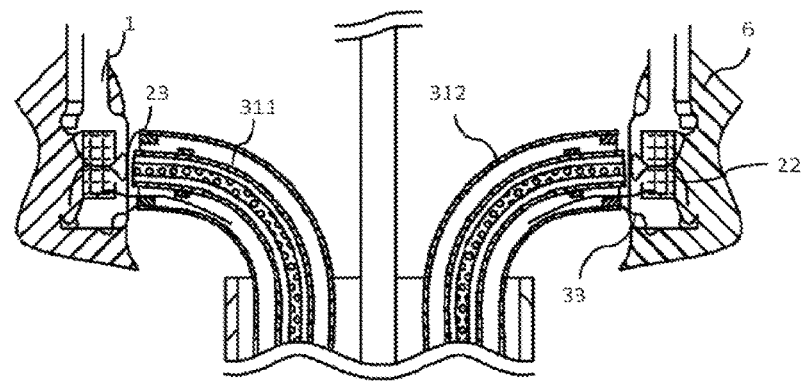

As shown in FIGS. 1a-1d and FIGS. 2a-2g, the implant with anchoring device for heart valve disease of the present invention, comprises a cardiac valve prosthesis 1, two sets of anchoring needles 2, two sets of anchoring needle releasing devices 3 and a delivery system 4. As shown in FIG. 1a, two sets of anchoring needle releasing devices are distributed symmetrically. As shown in FIG. 1b, the cardiac valve prosthesis 1, which is a replacement prosthesis for mitral valve, comprises a frame 11, leaflet 12 and anchoring regions 13. The frame 11 is formed by NI-TI shape memory alloy tubing through cutting and pre-heat-shaping process. The leaflet 12 is firmly fixed on the frame 11. The leaflet 12 is made of porcine pericardium. The anchoring regions 13 are made of polyester membrane and are fixed at the proximal end of the cardiac valve prosthesis 1. As shown in FIG. 1c, the anchoring needle 2 is made of NI-TI shape memory alloy wire with a diameter of 0.4 mm. The most distal end 21 of the anchoring needle 2 is sharp, and the distal section 22 of the anchoring needle is a bifurcated double hook, wherein, each hook is pre-formed into an arc with a radius of 3 mm. The proximal end of the anchoring needle 2 is provided with an anti-disengagement end 23, which is formed by further extending, winding and heat setting of the anchoring needle 2. The anti-disengagement end 23 is heat set to have a maximum width of 1.0 mm. When the anchoring needle 2 is pre-disposed into the distal section of the delivery tube 31, the anchoring needle 2 is in a stretched state as shown in FIG. 1d. In another embodiment (not shown), the distal section 22 of the anchoring needle is cut to have an arc with a radius of 3 mm; the anchoring needle is made of elastic alloy; when the anchoring needle is pushed out of the delivery tube, the distal section 22 of the anchoring needle is restored to have the preset arc shape. As shown in FIG. 1a, the anchoring needle releasing device comprises a delivery tube 31 and a shaft 32. As shown in FIGS. 1a and 2b, the delivery tube 31 is detachably connected to the cardiac valve prosthesis 1 through a connecting wire 33. The delivery tube 31 comprises two layers of tubes, wherein, the inner layer tube 311 has an internal diameter of 1.0 mm and is disposed inside the outer layer tube 312. One part of the distal section of the inner layer tube 311 extends out of the outer layer tube 312. One end of the connecting wire 33 is fixed at the distal section of the outer layer tube 312; another end of the connecting wire 33 goes through the cardiac valve prosthesis 1 and is winded back and clamped between the distal section of the inner layer tube 311 and the distal section of the outer layer tube 312. An outer bump made of stainless steel tube is welded at the outer side of the distal section of the inner tube 311, and an inner bump made of stainless steel tube is welded at the inner side of the distal section of the outer tube 312, thereby realizing the clamping function. As shown in FIG. 2a, the delivery system 4 known in the prior art, comprises a tip 41, an outer sheath tube 42, a sheath core 44, and an operating member 43. The sheath core 44 is arranged inside the outer sheath tube 42. The distal end of the sheath core 44 is fixedly connected to the tip 41; the proximal end of the sheath core 44 is fixedly connected to the operating member 43; the cardiac valve prosthesis 1 and the anchoring needle releasing device 3 are arranged between the outer sheath tube 42 and the sheath core 44. Two sets of anchoring needle releasing devices 3 are arranged symmetrically relative to the sheath core 44. The proximal end of the inner layer tube 311 and the proximal end of the outer layer tube 312 are fixedly connected to the operating member 43 of the delivery system 4. As shown in FIG. 2b, the connecting wire 33 is formed by winding a plurality of strands of stainless steel wires. The anchoring needle 2 is pre-placed inside the distal section of the inner layer tube 311 of the delivery tube 31 in an extended state. Because of the super elasticity of the nickel-titanium alloy, the anti-disengagement end 23 of the anchoring needle 2 is also pre-placed inside the distal section of the inner layer tube 311 of the delivery tube 31. The distal section of the anchoring needle releasing device 3 is in a preset shape, so that, before the anchoring needle is moved, the distal section of the delivery tube 31 can bend wholly or partially, and so that the most distal end of the delivery tube 31 presses tightly against the cardiac valve prosthesis 1 or against the autogenous tissue. As shown in FIGS. 2b-2c, the proximal sections of the delivery tubes 31 are rigid, while the distal sections 3112 and 3122 of the delivery tubes 31 can bend wholly or partially. The bendable parts of the delivery tubes 31 are bent sections 31121, 31221, and the most distal ends of the delivery tubes 31 are provided with rigid sections 31122, 31222. The length of each of the rigid sections 31122, 31222 is greater than the full length of the anchoring needle. The bent sections 31121, 31221 are made of stainless steel tube segments with slits. As shown in FIG. 2d, the length d from the most distal end of the delivery tube 31 to the most proximal end of the bent section 31121 or 31221 is larger than ⅙ of the circumference of a circle formed by the minimum radius r of the native heart valve tissue annulus of a patient. In the plane of the cross section of the valve tissue annulus, the minimum radius r is defined as the shortest distance from the valve tissue annulus to the centre of the cross section of the valve tissue annulus. As shown in FIGS. 2d-2f, the shaft 32 is made of shape memory alloy wire and is pre-shaped by heating so that the distal section of the shaft has a certain angle. When the shaft 32 pushes the anchoring needle, the shaft 32 can restore its shape of an arc, which is ⅙ of the circle formed by the minimum radius r of the native heart valve tissue annulus. The shaft 32 is placed inside the inner layer tube 311 of the delivery tube 31, and the anchoring needle 2 is disposed beside the distal end of the shaft 32. The proximal end of the shaft 32 is fixedly connected to the operating member 43 of the delivery system 4. The distal section 322 of the shaft 32, which has a pre-formed shape, can drive the distal section of the delivery tube 31 to bend.

Figure 2G:
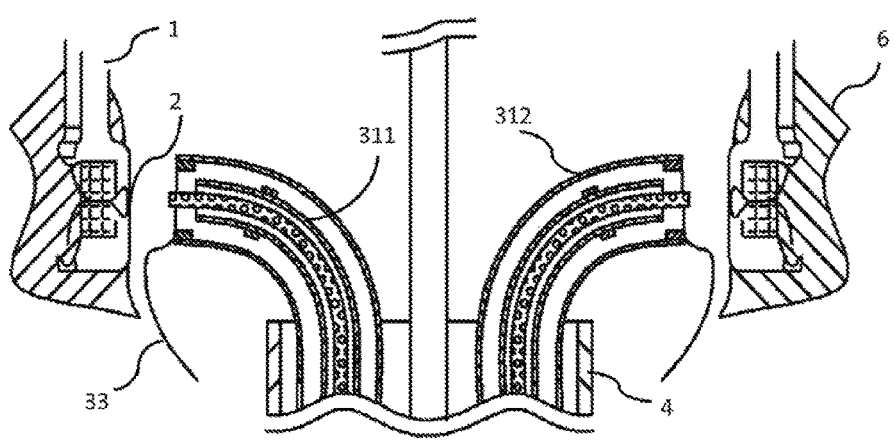

The steps for operating the implant with anchoring device for heart valve disease are as follows: as shown in FIGS. 2a-2b, the cardiac valve prosthesis 1, the anchoring needle 2 and the anchoring needle releasing device 3 are pressed and held radially inside the outer sheath tube 42. As shown in FIG. 1a, the cardiac valve prosthesis 1, the anchoring needle 2 and the anchoring needle releasing device 3 are sent into the heart atrium 5 through the cardiac apex approach. As shown in FIG. 2d, the cardiac valve prosthesis 1 and the anchoring needle releasing device 3 are released by retracting the outer sheath tube 42; at this moment, the distal section of the delivery tube 31 bends along with the distal section of the shaft 32, thereby restoring the preset shape of the shaft 32; the distal end of the delivery tube 31 presses perpendicularly against the tough piercing position and limits the piercing path, thereby the positioning operation is completed. As shown in FIG. 2e, the anchoring needle 2 is released by pushing the shaft 32; the most distal end 21 of the anchoring needle 2 penetrates the anchoring region 13, goes through the frame 11 and pierces the autogenous tissue 6. As shown in FIG. 2f, after the anchoring needle 2 is pushed out of the delivery tube 31, the distal section 22 of the anchoring needle 2 can restore the preset shape as a bifurcated double hook arc with a diameter of 3 mm. The diameter of 3 mm can ensure the anchoring needle 2 not to hurt the coronary artery; then the inner layer tube 311 of the delivery tube 31 is retracted, thereby releasing the anti-disengagement end 23 of the anchoring needle 2, and at the same time, unclamping the detachable connection of the connecting wire 33; at this moment, the anti-disengagement end 23 of the anchoring needle restores its preset shape, and the cardiac valve prosthesis 1 is disposed and firmly fixed between the autogenous tissue 6 and the anti-disengagement ends 23 of the anchoring needles 2. As shown in FIG. 2g, the inner layer tube 311 of the delivery tube is further retracted to further release one end of the connecting wire 33; then the outer layer tube 312 of the delivery tube or the delivery system 4 is retracted, enabling the connecting wire 33 to be extracted from the cardiac valve prosthesis 1 so as to complete the process of detaching the detachable connection between the delivery tube and the cardiac valve prosthesis; the cardiac valve prosthesis 1 is firmly fixed on the autogenous tissue 6 after the anchoring needle releasing device 3 and the delivery system 4 are finally retracted.

The Second Embodiment

Figure 3A:
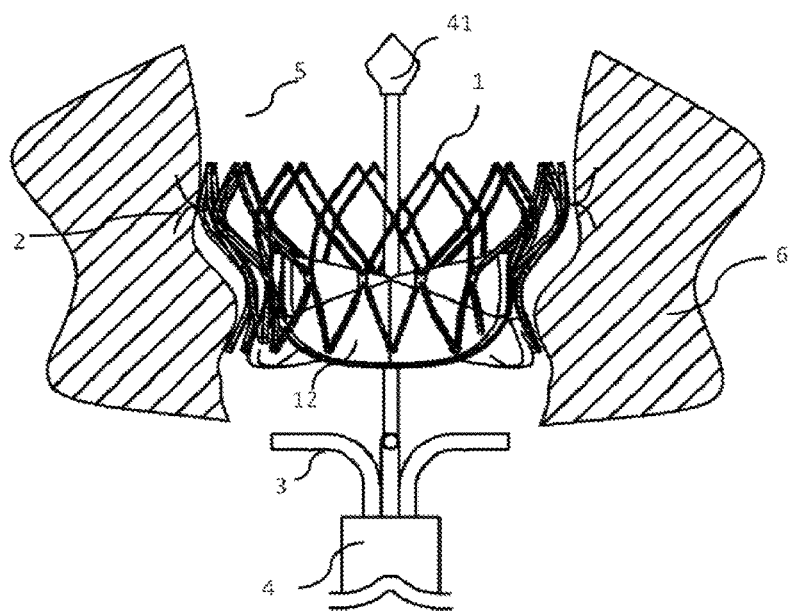
Figure 3B:
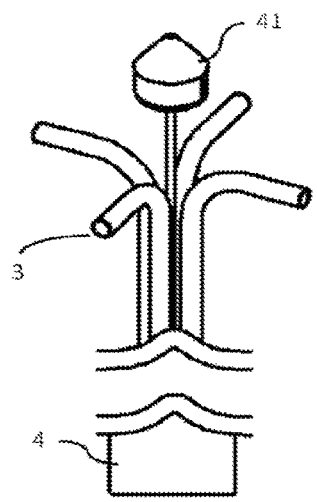
Figure 3C:
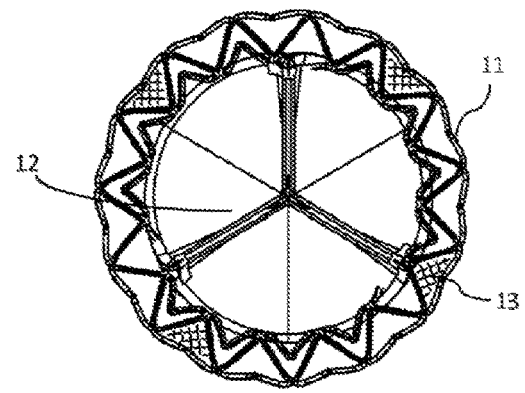
Figure 3D:
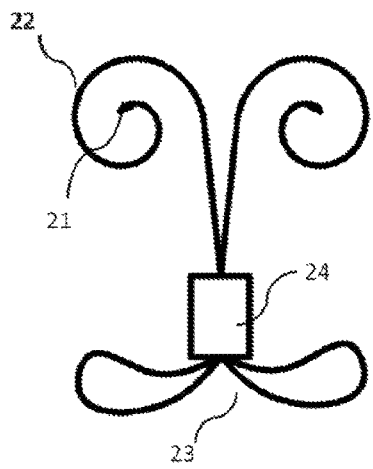
Figure 3E:
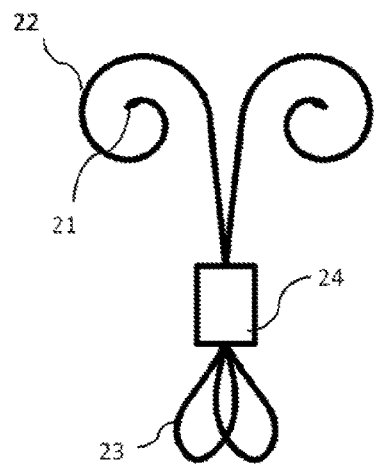
Figure 4A:
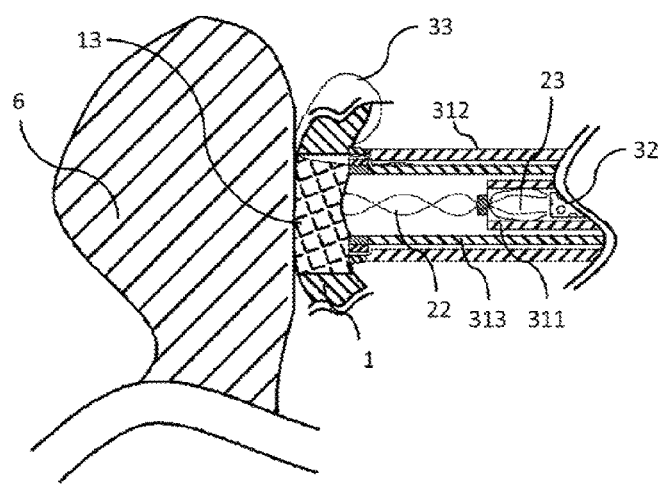
Figure 4B:
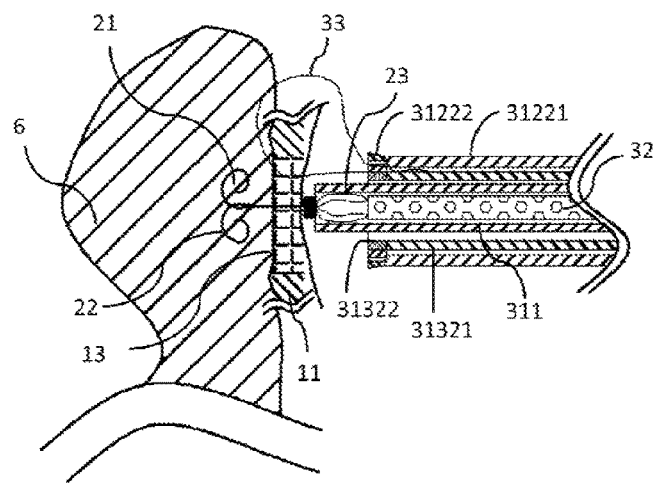

As shown in FIGS. 3a-3e, the implant with anchoring device for heart valve disease of the present invention comprises a cardiac valve prosthesis 1, four sets of anchoring needles 2, four sets of anchoring needle releasing devices 3 and a delivery system 4. As shown in FIG. 3a-3c, the cardiac valve prosthesis 1, which is a replacement prosthesis for tricuspid valve, is applicable to the tricuspid valve replacement surgery through the cardiac apex approach. Four sets of anchoring needle releasing devices 3 are evenly and circumferentially distributed. The second embodiment differs from the first embodiment in that: the valve 12 is made of polymer film; the anchoring positions, namely the anchoring regions 13, are disposed proximally to the heart atrium 5. As shown in FIG. 3d, the anchoring needle 2 is made of shape memory nickel-titanium wire with a diameter of 0.35 mm. The most distal end 21 of the anchoring needle 2 is sharp, and the distal section 22 of the anchoring needle 2 is preset to be spiral-shaped. The proximal end of the anchoring needle 2 is provided with an anti-disengagement end 23. The anti-disengagement end 23 is clamped and fixedly connected to the anchoring needle 2 by a stainless steel tube 24. The anti-disengagement end is formed by winding shape memory nickel-titanium wire with a diameter of 0.2 mm and is pre-shaped by heating. When the anti-disengagement end is pre-placed inside the delivery tube, the anti-disengagement end is in a stretched state, and the shape of the anti-disengagement end 23 is shown in FIG. 3e. When the anti-disengagement end restores to its preset shape formed by heating, the shape of the anti-disengagement end 23 is shown in FIG. 3d. As shown in FIG. 4a, the delivery tube 31 comprises three layers of tubes, wherein, the innermost layer tube 311 is disposed inside the middle layer tube 313; the middle layer tube 313 is disposed inside the outer layer tube 312. One end of the connecting wire 33 is fixed at the distal section of the middle layer tube 313; another end of the connecting wire 33 goes through the cardiac valve prosthesis 1 and is winded back and clamped between the distal section of the middle layer tube 313 and the distal section of the outer layer tube 312. The connecting wire 33 is formed by winding a single strand of super elastic nickel-titanium alloy wire. The inner layer tube 311 is made of hollow woven stainless steel cable, and the whole inner layer tube is bendable. As shown in FIG. 4b, the distal section of the middle layer tube 313 is bendable wholly, and the bendable part of the middle layer tube 313 is the bent section 31321. The most distal end of the middle layer tube 313 is provided with a rigid section 31322, which is made of stainless steel. The length of the rigid section 31322 is one tenth of the full length of the anchoring needle. An outer bump made of stainless steel tube is fixed at the outer side of the rigid section 31322. The bent section 31321 is made of bendable polymer tube reinforced by metal wire. The distal section of the outer layer tube 312 is bendable wholly. The bendable part of the outer layer tube 312 is the bent section 31221. The most distal end of the outer layer tube 312 is provided with a rigid section 31222, which is made of platiniridium ring and can be used as the mark point for localization. The bent section 31221 is made of bendable polymer tube reinforced by metal wire. As shown in FIG. 4a, the proximal section of the middle layer tube 313 and the proximal section of the outer layer tube 312 are made of stainless steel tubes. The proximal ends of three layers of tubes are fixedly connected to the operating member (not shown) of the delivery system 4 respectively. The anchoring needle 2 is pre-placed inside the middle layer tube 313, and the distal section 22 of the anchoring needle is disposed inside the distal section of the middle layer tube 313 and disposed outside the distal section of the inner layer tube 311. The anti-disengagement end 23 is disposed inside the distal section of the inner layer tube 311. The distal section 322 of the shaft 32 has a preset shape and can bend wholly, and is pre-placed inside the inner layer tube 311 of the delivery tube 31. The anti-disengagement end 23 is disposed beside the distal end of the shaft 32.

Figure 4C:
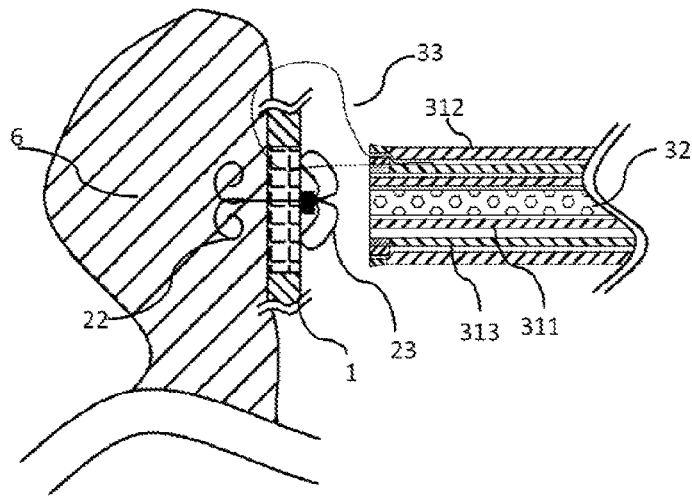
Figure 4D:
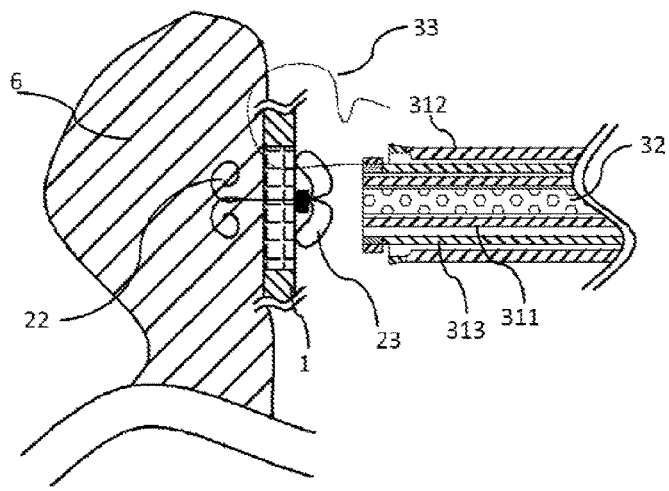
Figure 4E:
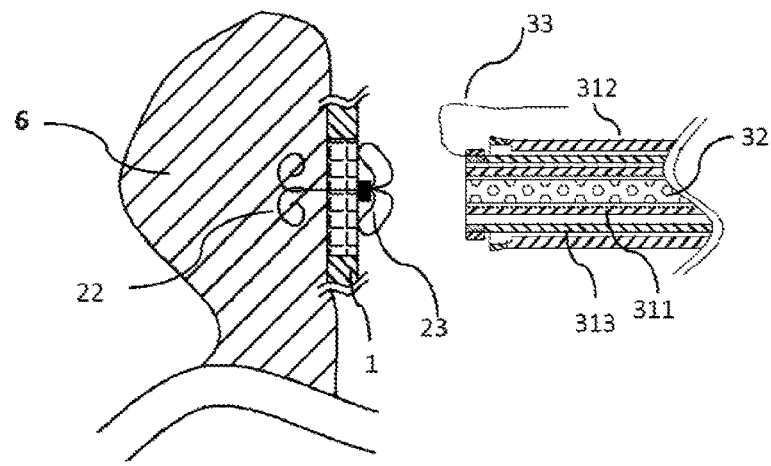
Figure 4F:
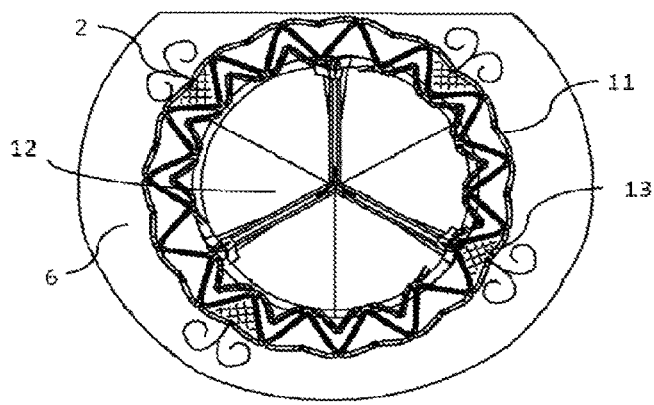

As shown in FIGS. 4a-4b, the operation steps of the second embodiment differ from those of the first embodiment in that: after releasing the cardiac valve prosthesis 1 and the anchoring needle releasing device 3 (not shown) through retracting the outer sheath tube 42, operating the operating member of the delivery system 4 to push the inner layer tube 311 of the delivery tube 31 and the shaft 32. At this moment, as the autogenous tissue 6 is elastic, under action of the push force, the anti-disengagement end 23 of the anchoring needle and the distal section of the inner layer tube 311 of the delivery tube 31 can be pushed out of the distal ends of the middle layer tube 313 and the outer layer tube 312. At this moment, the most distal end 21 of the anchoring needle 2 penetrates the anchoring region 13, goes through the frame 11 and pierces the autogenous tissue 6. After the anchoring needle 2 is pushed out of the delivery tube 31, the distal section 22 of the anchoring needle 2 restores its preset shape. As shown in FIG. 4c, through controlling the operating member of the delivery system 4, the shaft 32 is kept still, the inner layer tube 311 is retracted and the anti-disengagement end 23 is released to restore its preset shape formed by heating, thereby forcing the cardiac valve prosthesis 1 to be fixed tightly on the autogenous tissue 6. As shown in FIGS. 4d-4e, the outer layer tube 312 is retracted, the connecting wire 33 is released, the anchoring needle releasing device 3 and the delivery system 4 are retracted, so as to complete the implanting process. Finally, as shown in FIG. 4f, the cardiac valve prosthesis 1 is firmly fixed on the autogenous tissue 6 by four anchoring needles 2.

The Third Embodiment

Figure 5A:
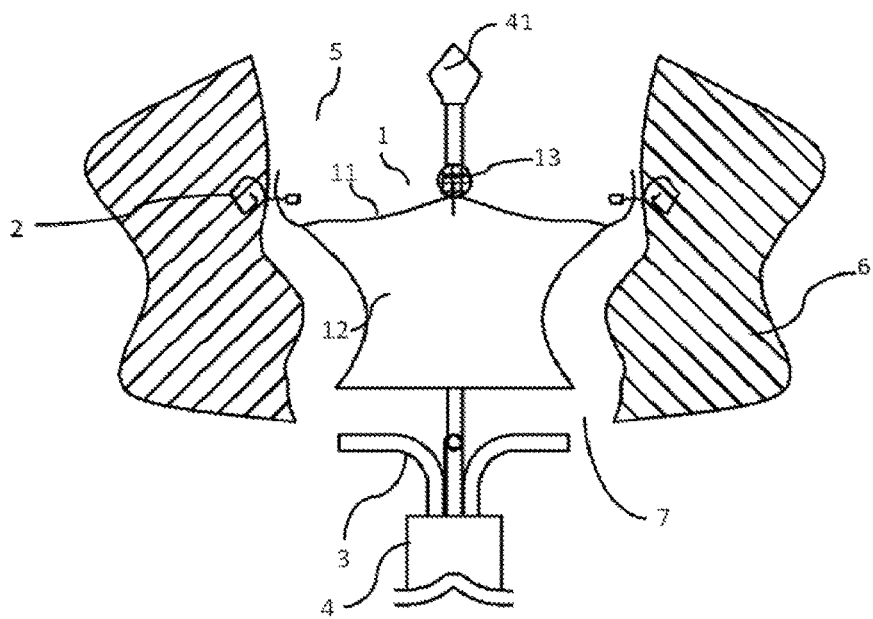
Figure 5B:
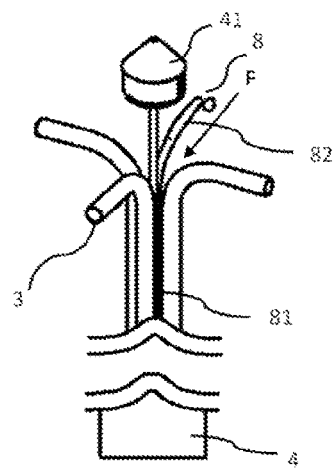

As shown in FIGS. 5a-5b, the implant with anchoring device for heart valve disease of the present invention comprises a cardiac valve prosthesis 1, three sets of anchoring needles 2, three sets of anchoring needle releasing devices 3, a delivery system 4, and a set of supporting device 8.

Figure 5C:
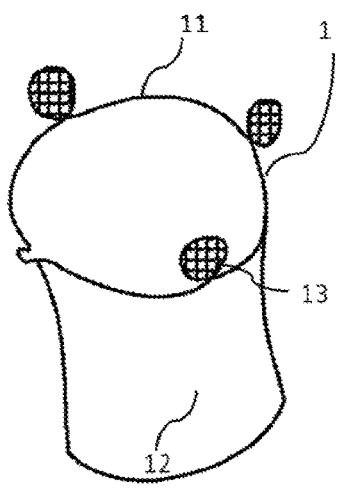
Figure 5D:
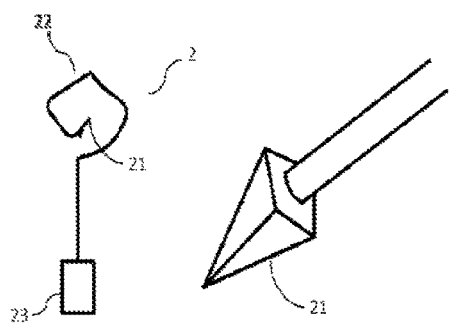
Figure 5E:
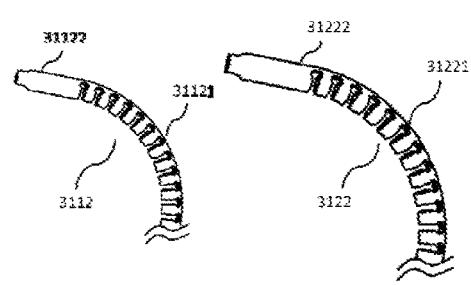
Figure 5F:
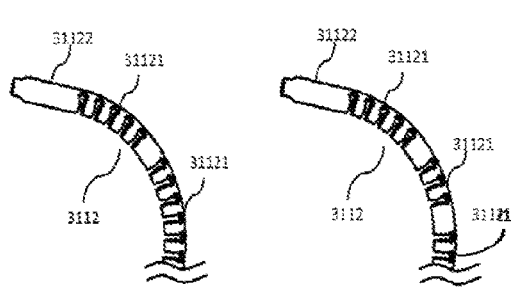
Figure 5G:
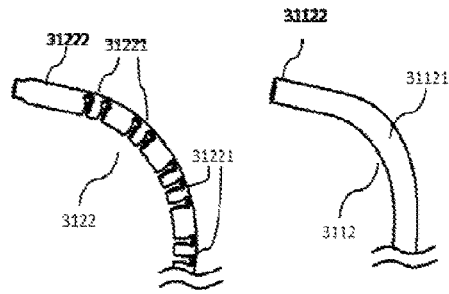
Figure 6A:
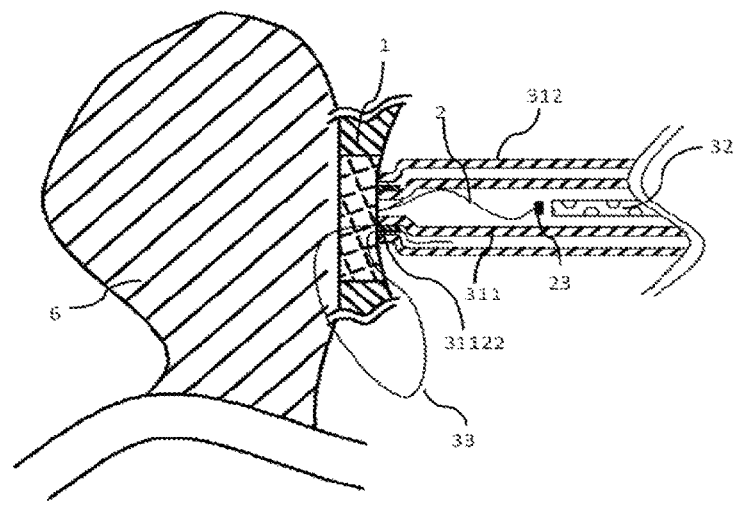

In some embodiments, as shown in FIGS. 5a and 5c, the cardiac valve prosthesis 1, which is a prosthesis for repairing the mitral valve, is applicable to the mitral valve repair surgery through the cardiac apex approach. The third embodiment differs from the second embodiment in that: the frame 11 is formed by NI-TI shape memory alloy wires through winding and pre-heat-shaping process; the leaflet 12 is made of polymer film and is fixed on the frame 11, and further extends to the heart chamber 7; the leaflet 12 moves along with the native heart valve, so as to prevent the native heart valve from entering the heart atrium 5 due to the prolapse of the chordae tendineae when the native heart valve is closed, thereby preventing regurgitation. As shown in FIG. 5a, the anchoring positions of the cardiac valve prosthesis 1 are located proximal to the heart atrium 5. As shown in FIG. 5b, the supporting device 8 is made of shape memory nickel-titanium alloy wire with a diameter of 1 mm. The proximal end 81 of the supporting device 8 is fixedly connected to the operating member of the delivery system 4. The implant with anchoring device for heart valve disease further comprises a supporting device and an operating member for the supporting device; the operating member for the supporting device is fixedly connected to a proximal end of the supporting device. The distal section 82 of the supporting device 8 is bendable and has the same preset shape as that of the shaft 32, so that the distal section 82 of the supporting device 8 can press against the autogenous tissue 6 when the supporting device 8 is released. Due to the elasticity of the nickel-titanium alloy, when the distal section 82 of the supporting device 8 presses against the autogenous tissue 6 heavily, the autogenous tissue 6 exerts an opposite force F on the distal section 82. As the supporting device 8 directly or indirectly contacts with the delivery tube 31, for example, the supporting device 8 is arranged opposite to the delivery tube 31 at an angle of 180 degrees, the supporting device 8 transfers the opposite force F to the delivery tube 31 arranged on the opposite side of the supporting device or the supporting device 8 and the delivery tube 31 are evenly and circumferentially distributed, the supporting device 8 transfers component force of the opposite force F to the delivery tube which contacts the supporting device. The supporting force exerted by the supporting device 8 ensures that the delivery tube 31 which directly or indirectly contacts with the supporting device continuously pressing against the autogenous tissue 6, thereby limiting the piercing path and ensuring the anchoring needle 2 to pierce the autogenous tissue. In one embodiment, the anchoring needles 2 and the anchoring needle releasing devices 3 are not one-to-one in number; the number of the anchoring needle releasing devices 3 is larger than the number of the anchoring needles 2, and the anchoring needle releasing devices 3 with no anchoring needles 2 placed inside can act as the supporting device 8. As shown in FIGS. 6f-6i, in another embodiment, the delivery system comprises a tip 41, an outer sheath tube 42, a sheath core 44, and an operating member 43. The sheath core 44 is arranged inside the outer sheath tube 42. The distal end of the sheath core 44 is fixedly connected to the tip 41; the proximal end of the sheath core 44 is fixedly connected to the operating member 43; the cardiac valve prosthesis (not shown), the anchoring needle releasing device 3, and the supporting device 8 are arranged between the outer sheath tube 42 and the sheath core 44. The distal section 82 of the supporting device 8 is fixedly connected to the tip 41 of the delivery system (as shown in FIG. 6f); or the proximal end 81 of the supporting device 8 is fixedly connected to the operating member 43 of the delivery system (as shown in FIG. 6h); or the proximal end of the supporting device 8 is fixedly connected to the operating member 43 of the delivery system, and the distal end of the supporting device 8 is fixedly connected to the tip 41 of the delivery system (not shown). As the supporting device 8 fills the inner space of the outer sheath tube 42 (as shown in FIGS. 6g and 6i, which are schematic sectional views of the supporting device 8 in the outer sheath tube 42 respectively), when the anchoring needle releasing device 3 is released, it will not shake in the outer sheath tube 42. What's more, the supporting device 8 exerts supporting force on the anchoring needle releasing device 3, and the supporting force can resist the acting force exerted on the anchoring needle releasing device 3 by the autogenous tissue, thereby increasing the success rate of piercing. When a plurality of sets of anchoring needle releasing devices 3 are provided in the outer sheath tube 42, if there is no spare space for arranging the supporting device 8, the sheath core 44 provided inside the outer sheath tube 42 acts as the supporting device 8. As shown in FIGS. 6j-6k, in one embodiment, the implant with anchoring device for heart valve disease comprises a cardiac valve prosthesis, two sets of anchoring needles, two sets of anchoring needle releasing devices 3 and a delivery system, and two sets of supporting devices 8. The two sets of supporting devices 8 are adjacent. The two sets of supporting devices 8 and the two sets of anchoring needle releasing devices 3 are evenly and circumferentially distributed. The delivery system comprises a tip 41, an outer sheath tube 42 (not shown), a sheath core 44, and an operating member 43 (not shown). The sheath core 44 is arranged inside the outer sheath tube. The distal end of the sheath core 44 is fixedly connected to the tip 41; the proximal end of the sheath core 44 is fixedly connected to the operating member; before releasing, the cardiac valve prosthesis (not shown), the anchoring needle releasing device 3, and the supporting devices 8 are arranged between the outer sheath tube and the sheath core 44. The supporting devices 8 are made of stainless steel tubes. The proximal end 81 of the supporting device 8 is fixedly connected to the operating member of the delivery system; the distal section 82 of the supporting device 8 has slits, which enables the distal section 82 of the supporting device 8 to bend. The distal section 82 of the supporting device 8 is movably connected to a rigid supporting rod 822, and the distal end of the supporting rod 822 is movably connected to the tip 41. In one embodiment, as shown in FIG. 6j, the junction of the distal section 82 of the supporting device and the supporting rod 822 is a boundary line. The positions of the slits in the section 821 at the far side of the boundary line are opposite to those of the slits in the section 823 at the near side of the boundary line, so as to form an S-shaped bend. After the anchoring needle releasing device and the supporting devices are released, the distal sections 82 of the supporting devices bend at the actions of the tip 41 and supporting rods 822. Firstly, the section 823 at the near side of the boundary line bends; after the section 821 at the far side of the boundary line contacts the autogenous tissue, the section 821 at the far side of the boundary line bends gradually because the section 821 is provided with slits, thereby pressing against the autogenous tissue tightly. Due to the elasticity of the autogenous tissue, when distal sections 82 of the supporting devices press against the autogenous tissue tightly, the autogenous tissue acts an opposite force F on the distal sections 82. As the supporting device 8 directly or indirectly contacts the delivery tube 31, for example, the supporting device 8 and the delivery tube 31 are evenly and circumferentially distributed, the supporting device 8 transfers the opposite force F to the delivery tube arranged on the opposite side of the supporting device. The supporting force provided by the supporting device 8 ensures that the delivery tube 31 which indirectly contacts the supporting device continues pressing against the autogenous tissue 6, thereby limiting the piercing path and ensuring the anchoring needle 2 to pierce the autogenous tissue. In one embodiment, the distal section of the delivery tube 31 is movably connected to a rigid supporting rod 822, and the distal end of the rigid supporting rod 822 is movably connected to the tip 41, so as to control the bending angle the distal section of the delivery tube 31 better. As shown in FIG. 5d, the anchoring needle 2 is made of shape memory nickel-titanium wire with a diameter of 0.5 mm. The most distal end 21 of the anchoring needle 2 is sharp and has a barb. The distal section 22 of the anchoring needle is pre-shaped to be a combined shape of arcs and straight lines. Or in another embodiment, the anchoring needle 2 is made of elastic alloy board and is pre-cut to be a shape as shown in the figure. The proximal end of the anchoring needle 2 is provided with an anti-disengagement end 23, which is made of nickel-titanium tubes and fixedly connected to the anchoring needle 2 through argon-arc welding. As shown in FIG. 6a, the delivery tube 31 comprises two layers of tubes, wherein, the inner layer tube 311 is disposed inside the outer layer tube 312. One end of the connecting wire 33 is fixed at the distal section of the inner layer tube 311; another end of the connecting wire 33 goes through the cardiac valve prosthesis 1 and is winded back and clamped between the distal section of the inner layer tube 311 and the distal section of the outer layer tube 312. The connecting wire 33 is made of flexible polymer strip. As shown in FIG. 5e, diameters of the distal ends of the inner layer tube 311 and the outer layer tube 312 are reduced. The distal section 3112 of the inner layer tube 311 and the distal section 3122 of the outer layer tube 312 have preset shapes or are pre-shaped, and can be partially bent, which enables the distal section 322 of the shaft 32 to bend according to the pre-formed shapes of the distal section 3112 of the inner layer tube 311 and the distal section 3122 of the outer layer tube 312. The bendable parts of the inner layer tube 311 and the outer layer tube 312 are bent sections 31121 and 31221 respectively, and the distal ends of the inner layer tube 311 and the outer layer tube 312 are provided with rigid sections 31122 and 31222. The length of each of the rigid sections 31122, 31222 is greater than half of the full length of the anchoring needle 2. In one embodiment, the bent sections 31121 and 31221 have slits, thereby realizing bend of the distal sections of the inner layer tube 311 and the outer layer tube 312. In other embodiments, as shown in FIGS. 5f-5g, the number of bent sections 31121 and 31221 can be greater than one, so as to realize partially bending. Or as shown in the figure at the right of FIG. 5g, the distal section 3112 of the inner layer tube 311 of the delivery tube, which is made of super elastic nickel-titanium tube pre-shaped by heating, comprises the bent section 31121 with a bent angle pre-formed by heating and a rigid section 31122 disposed at the distal end. As shown in FIG. 6a, an outer bump made of stainless steel tube, which is configured to fix the connecting wire 33, is provided at the outer side of the rigid section 31122. The anchoring needle 2 is pre-placed inside the inner layer tube 311, and the anti-disengagement end 23 is disposed beside the distal end of the shaft 32.

Figure 6B:
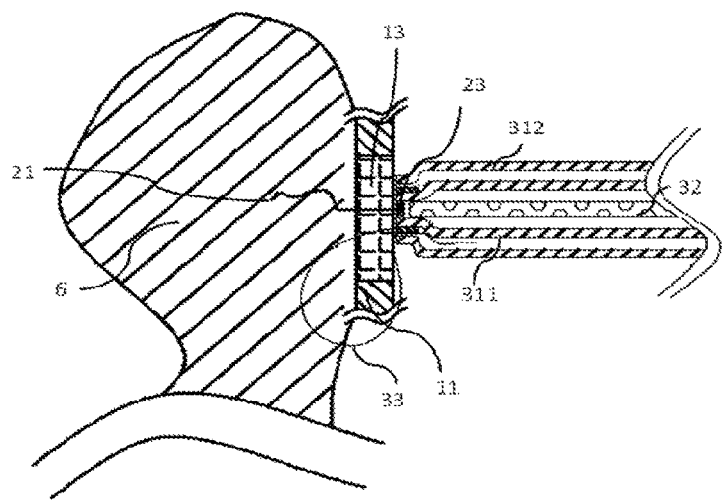
Figure 6C:
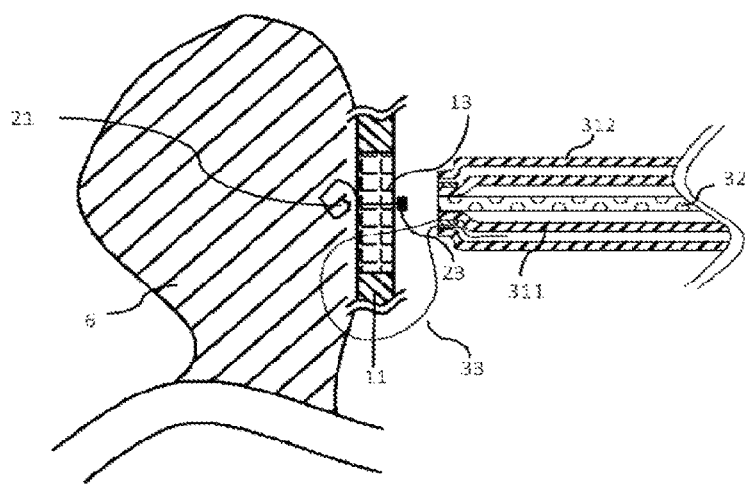
Figure 6D:
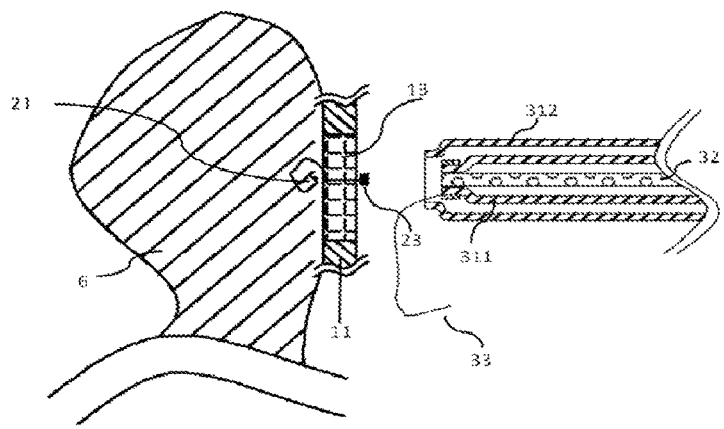
Figure 6E:
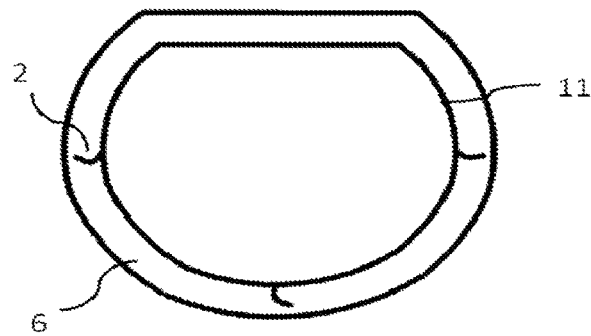
Figure 6F:
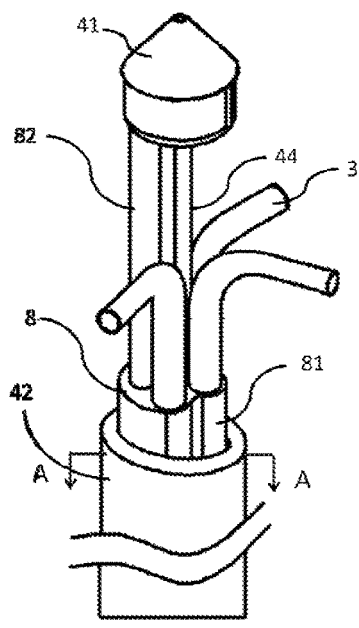
Figure 6G:
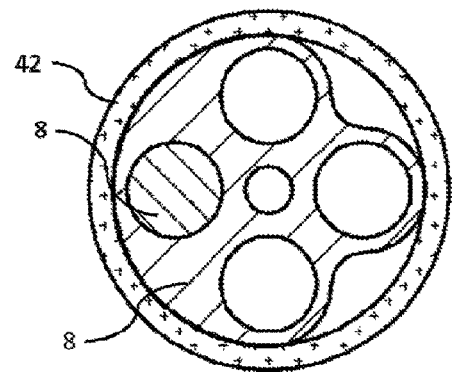
Figure 6H:
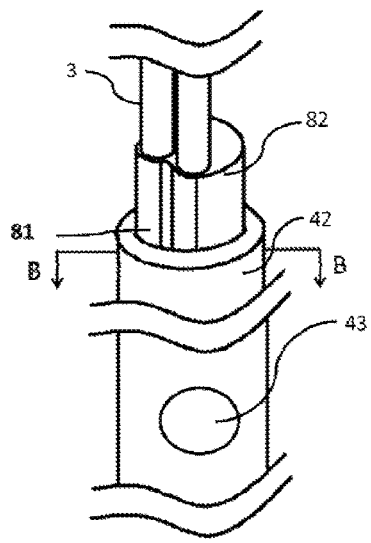
Figure 6I:
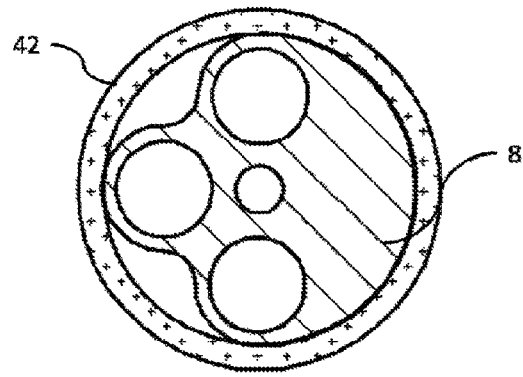
Figure 6J:
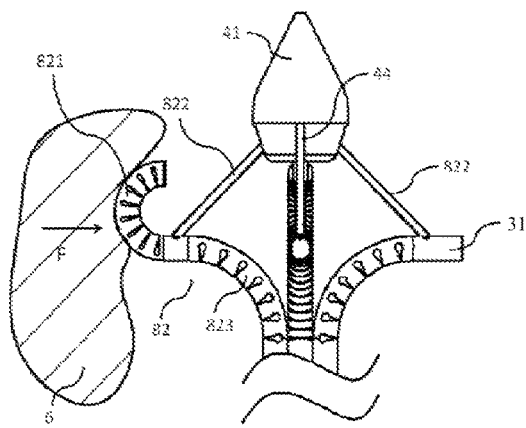
Figure 6K:
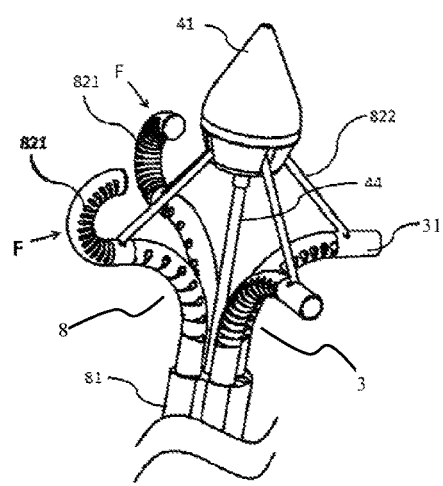

As shown in FIGS. 6a-6b, after releasing the cardiac valve prosthesis 1 and the anchoring needle releasing device (not shown) through retracting the outer sheath tube, operate the delivery system to push the shaft 32, so that the distal section of the anchoring needle 2 is pushed out of the delivery tube. The distal end 21 of the anchoring needle 2 penetrates the anchoring region 13, goes through the frame 11 and pierces the autogenous tissue 6. After the anchoring needle 2 is pushed out of the delivery tube, the distal section of the anchoring needle 2 is restored the preset shape. As shown in FIG. 6c, as the connecting wire 33 is loose, the frame 11 will have influence in retracting the delivery tube wholly, forcing the anti-disengagement end 23 to fall from the delivery system. At this moment, as shown in FIG. 6d, making use of the gap between the frame 11 and the inner layer tube 311 and the outer layer tube 312 of the delivery tube, and making use of the elasticity the autogenous tissue 6, through controlling the operating member of the delivery system, the outer layer tube 312 is pushed forwards to release the connecting wire 33; the inner layer tube 311 is further retracted to detach the connecting wire 33 from the frame 11; the anchoring needle releasing device and the delivery system are further retracted, thereby completing the implanting process. The final state is as shown in FIGS. 6e and 5c, the cardiac valve prosthesis 1 is fixed on the autogenous tissue 6 by three anchoring needles 2. The valve 12 moves along with the native heart valve to prevent regurgitation.

The Fourth Embodiment

Figure 7D:
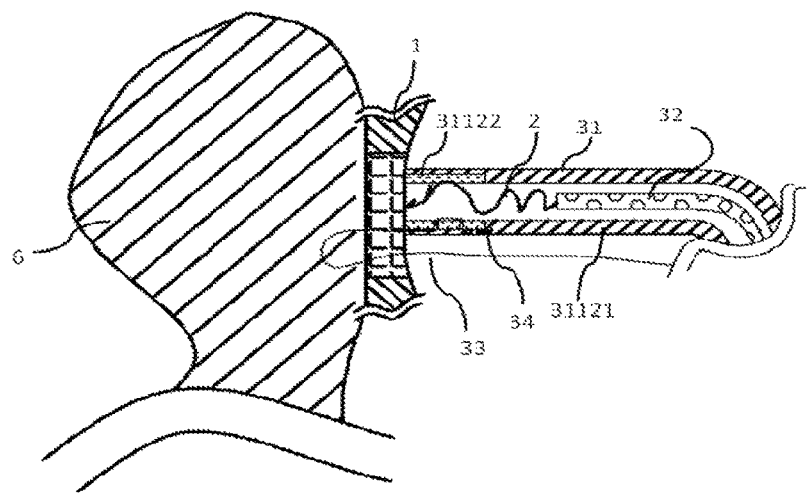
Figure 7E:
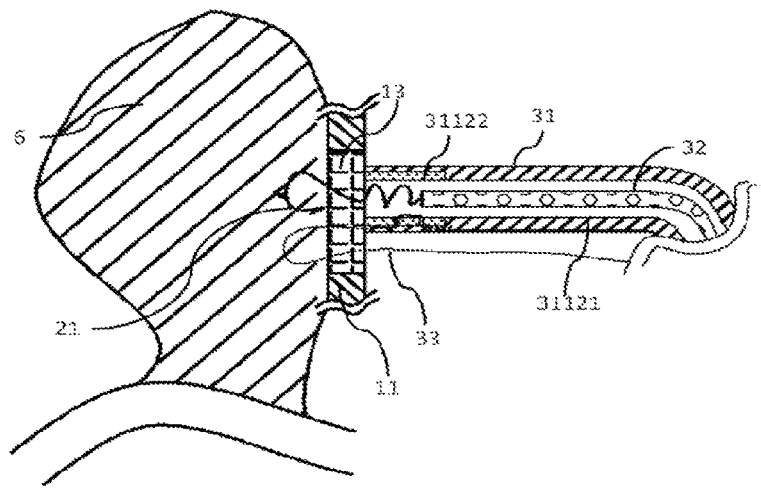
Figure 7F:
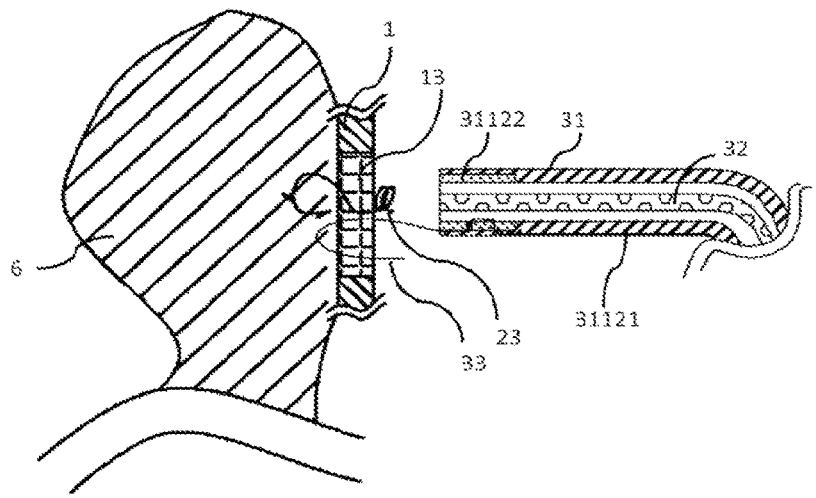
Figure 7G:
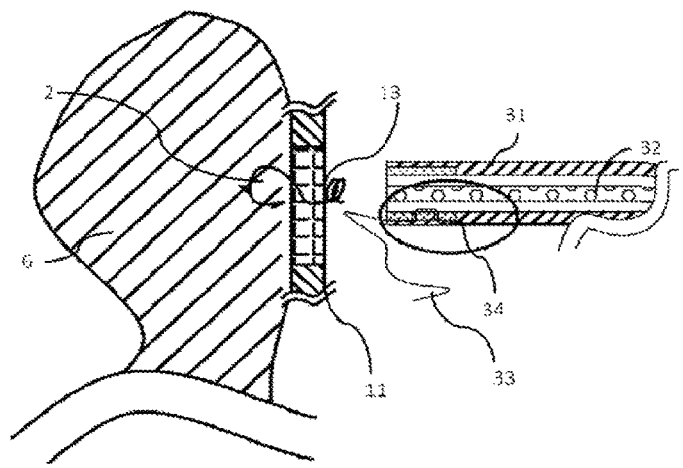
Figure 7H:
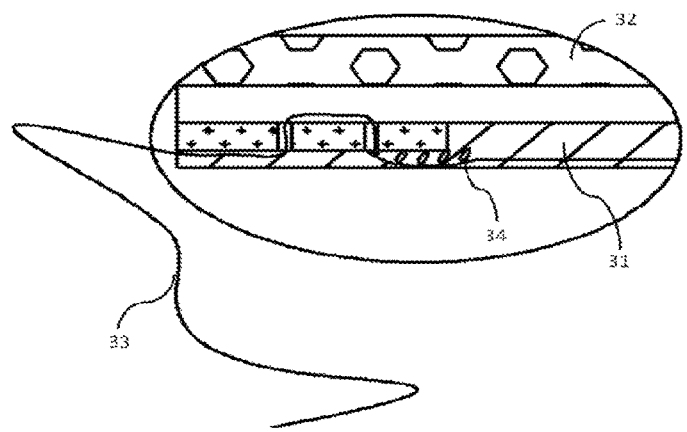

As shown in FIG. 7a, the implant with anchoring device for heart valve disease of the present invention comprises a cardiac valve prosthesis 1, two sets of anchoring needles 2, two sets of anchoring needle releasing devices 3, and a delivery system 4. As shown in FIGS. 7a-7b, the cardiac valve prosthesis 1, which is a replacement prosthesis for aortic valve, is applicable to the aorta replacement surgery through the cardiac apex approach. The fourth embodiment differs from the third embodiment in that: the frame 11 is formed by NI-TI shape memory alloy wires through winding and pre-heat-shaping process; the leaflet 12 is made of bovine pericardium and is fixed on the frame 11; the anchoring positions of the cardiac valve prosthesis 1 are located proximal to the aortic valve ring 9. As shown in FIG. 7c, the anchoring needle 2 is made of shape memory nickel-titanium wire with a diameter of 0.45 mm. The most distal end 21 of the anchoring needle 2 is sharp and has a plurality of barbs. The distal section 22 of the anchoring needle is pre-formed to have an arc shape. The proximal end of the anchoring needle 2 has an anti-disengagement end 23, which is formed by extending and winding the proximal end of the anchoring needle. As shown in FIG. 7d, the shaft 32 is made of stainless steel cables, and the delivery tube 31 is a single layer tube. As shown in FIG. 7a, the proximal section 3111 of the delivery tube 31 is a rigid stainless steel tube, and the proximal end of the delivery tube 31 is fixedly connected to the operating member of the delivery system 4. As shown in FIGS. 7a and 7d, the distal section 3112 of the delivery tube 31 has a preset shape, so that the distal section 3112 of the delivery tube 31 can bend wholly. The bendable part of the delivery tube 31 is the bent section 31121, and the most distal end of the delivery tube 31 is provided with the rigid section 31122. The bent section 31121 is a sterable sheath tube. The rigid section 31122 is made of a stainless steel tube, and the length of the rigid section is half of the length of the anchoring needle 2. The periphery of the rigid section 31122 is coated with polymers. The distal end of the rigid section 31122 is fixedly connected to a connecting wire 33; one end of the connecting wire 33 is wrapped in the polymers. The proximal end of the rigid section 31122 is connected to the distal end of the bent section 31121. The bent section 31121 is made of a polymer tube reinforced by a metal ring. The proximal end of the rigid section 31122 (or the distal end of the bent section 31121) is fixedly connected to controlling wire 34 needed for sterable sheath. As shown in FIG. 7h, the other end of the bend adjusting line 34 is fixedly connected to the operating member of the delivery system 4. The other end of the connecting wire 33 goes through the cardiac valve prosthesis 1 and is winded back and connected to the operating member of the delivery system 4. The connecting wire 33 is made of a plurality of strands of polymer wires. As shown in FIGS. 7d-7h, the operation steps of the fourth embodiment differs from the third embodiment in that: after the cardiac valve prosthesis 1 and the anchoring needle releasing device (not shown) are released through retracting the outer sheath tube, the delivery system is operated and the controlling wire 34 are adjusted, thereby adjusting the bent angle of the distal section of the delivery tube 31, so that the distal end (the exit of the anchoring needle) of the delivery tube 31 presses perpendicularly against the autogenous tissue 6 before the anchoring needle 2 is moved. At this moment, as shown in FIG. 7e, the shaft 32 is pushed to drive the anchoring needle 2 out of the distal end of the delivery tube 31; at this moment, the distal end 21 of the anchoring needle penetrates the anchoring region 13, goes through the frame 11 and pierces the autogenous tissue 6. After the anchoring needle 2 is pushed out of the delivery tube 31, the distal section 22 of the anchoring needle 2 restores its preset shape. The connection between the connecting wire 33 and the operating member is detached by controlling the operating member of the delivery system, the delivery tube 31 is retracted, and the anti-disengagement end 23 is released, as shown in FIG. 7f, so that the anti-disengagement end 23 restores the preset shape, thereby forcing the cardiac valve prosthesis 1 to be fixed tightly on the autogenous tissue 6. As shown in FIG. 7g, the detachable connection between the delivery tube 31 and the cardiac valve prosthesis 1 is released. The releasing device and the delivery system are further retracted, and the implanting process is completed.

Figure 7I:
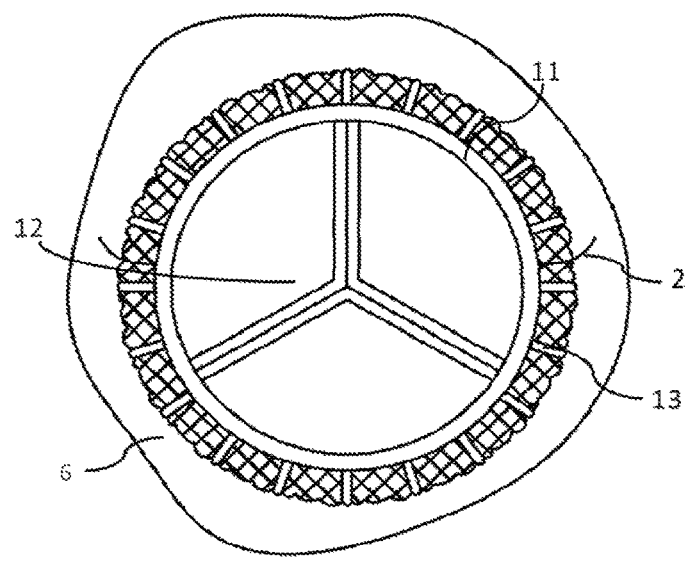

As shown in FIG. 7i, the cardiac valve prosthesis 1 is firmly fixed proximal to the aortic valve ring 9 by two anchoring needles 2 finally.

The Fifth Embodiment

Figure 8A:
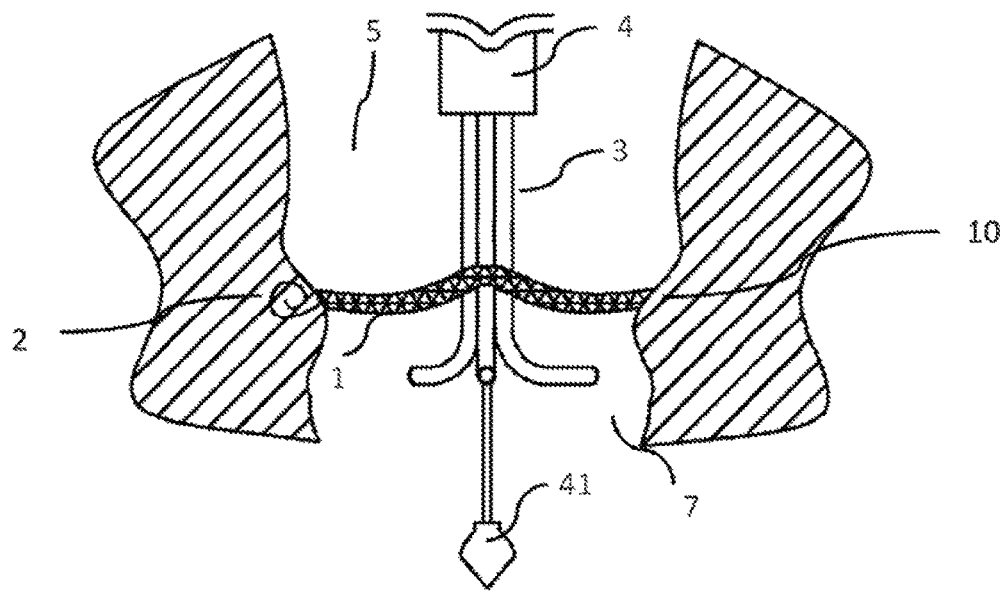
Figure 8B:
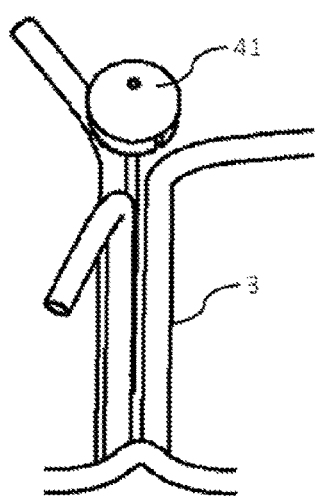
Figure 8C:
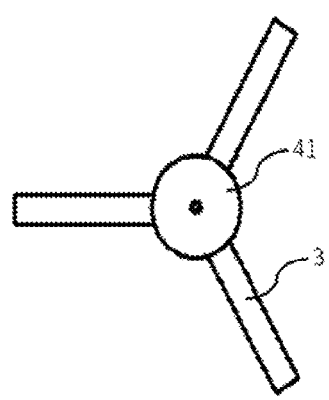

As shown in FIGS. 8a-8c, the implant with anchoring device for heart valve disease of the present invention comprises a cardiac valve prosthesis 1, three sets of anchoring needles 2, three sets of anchoring needle releasing devices 3, and a delivery system 4.

Figure 8D:
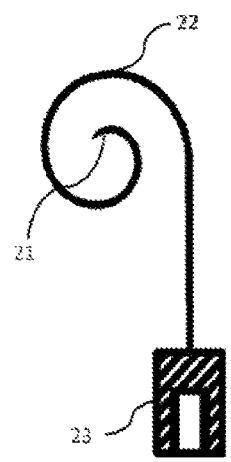
Figure 8E:
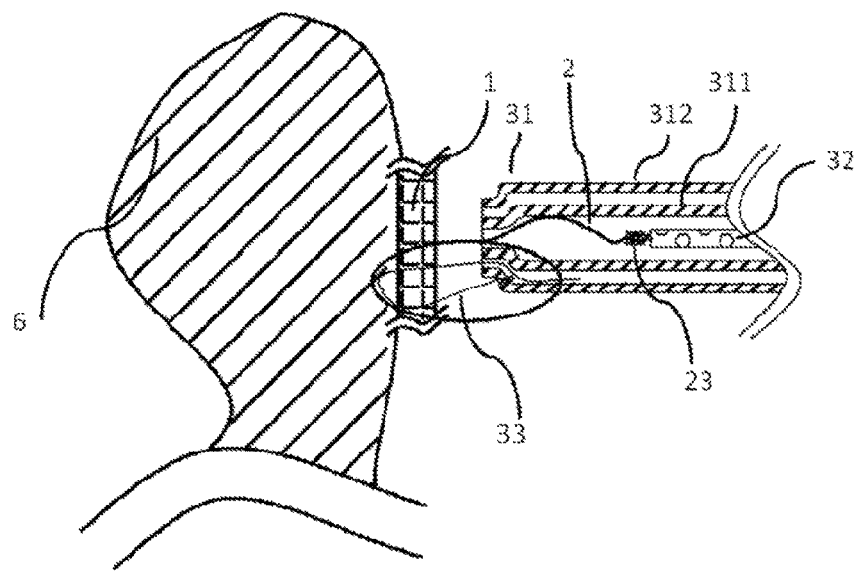
Figure 8F:
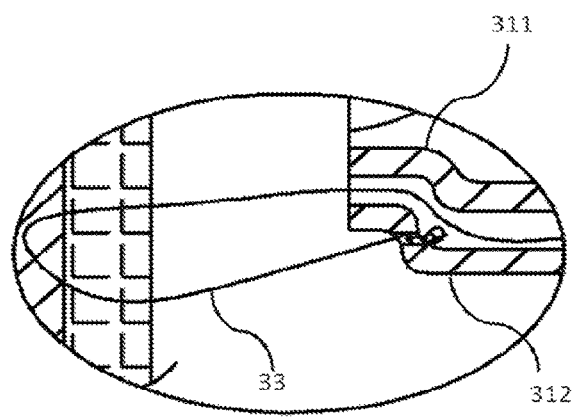
Figure 8G:
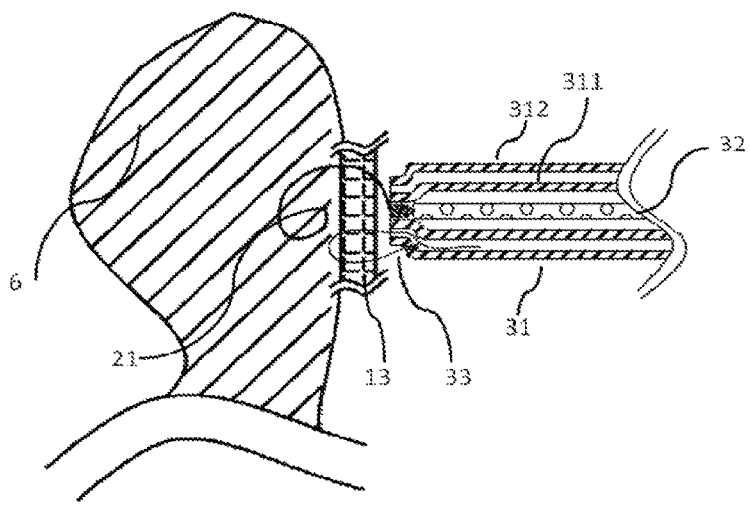
Figure 8H:
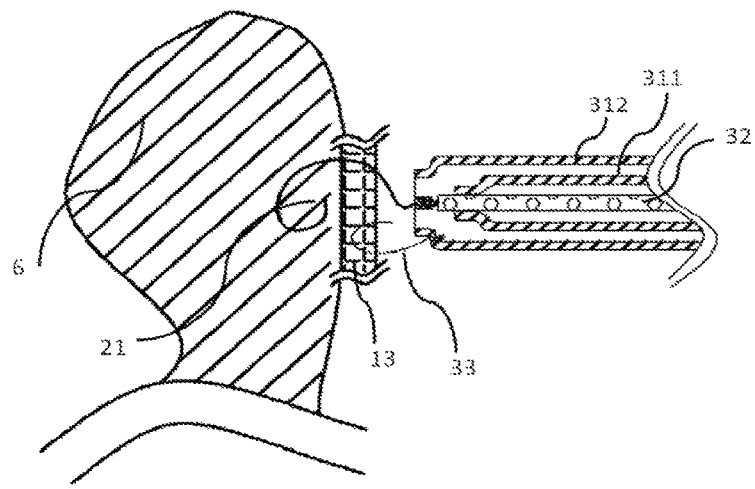
Figure 8I:
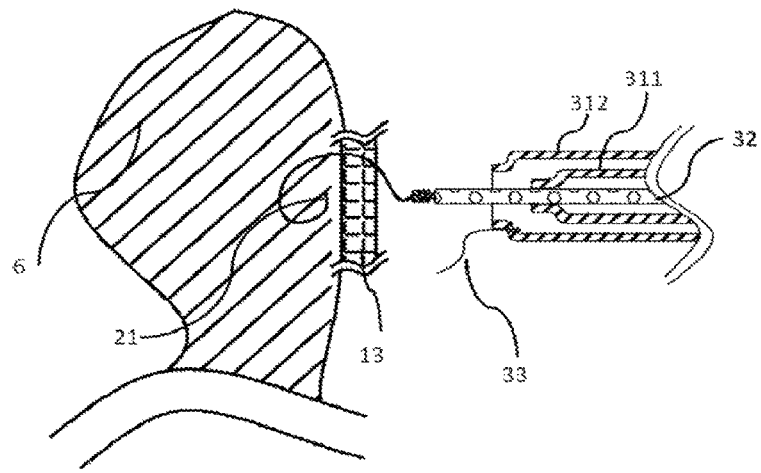
Figure 8J:
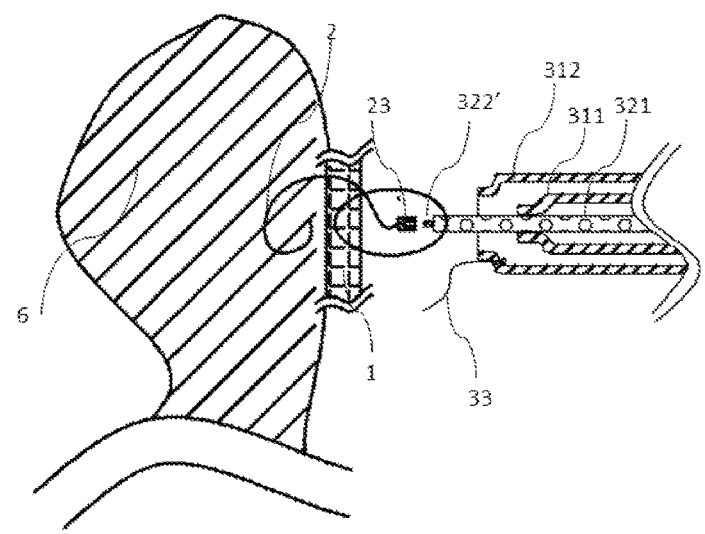

In some of the embodiments, as shown in FIG. 8a, the cardiac valve prosthesis 1 is used for mitral valve annuloplasty through the heart atrium 5 approaching to prevent cardiac valve regurgitation. The fifth embodiment differs from the fourth embodiment in that: the cardiac valve prosthesis 1 is fixed on the mitral valve annulus 10 by the anchoring needles 2. As shown in FIG. 8d, the anchoring needle 2 is made of shape memory nickel-titanium wire with a diameter of 0.35 mm. The distal section 22 of the anchoring needle is pre-formed to have an arc shape. The proximal end of the anchoring needle 2 is provided with an anti-disengagement end 23 with internal screw threads, which is made of stainless steel. As shown in FIGS. 8e-8f, the delivery tube 31 comprises two layers of tubes (311 and 312), wherein, the inner layer tube 311 is disposed inside the outer layer tube 312. One end of the connecting wire 33 is fixed at the distal end of the outer layer tube 312; another end of the connecting wire 33 goes through the cardiac valve prosthesis 1 and is winded back and clamped between the distal section of the inner layer tube 311 and the distal section of the outer layer tube 312. The connecting wire 33 is made of shape memory nickel-titanium wire with a diameter of 0.1 mm. The distal ends of the inner layer tube 311 and the outer layer tube 312 have reduced diameters. The distal section of the inner layer tube 311 and the distal section of the outer layer tube 312 have slits, thereby enabling the distal section of the inner layer tube 311 and the distal section of the outer layer tube 312 to bend wholly. The bendable parts of the inner layer tube 311 and the outer layer tube 312 are bent sections, and the most distal end of the delivery tube 31 is provided with a rigid section, whose length is greater than one third of the full length of the anchoring needle 2. An operating member of delivery tube is fixedly connected to the proximal end of the delivery tube 31. The inner layer tube 311 and the outer layer tube 312 are fixedly connected to the operating member of delivery tube respectively, or the proximal end of the delivery tube 31 is fixedly connected to the operating member of the delivery system 4. As shown in FIG. 8f, the distal section of the outer layer tube 312 has a hole, which is configured to fix the connecting wire 33. As shown in FIG. 8e, the anchoring needle 2 is pre-placed inside the inner layer tube 311, and the anti-disengagement end 23 is disposed beside the distal end of the shaft 32. As shown in FIG. 8j-8k, a metal head 322' with external screw threads is provided at the distal section of the shaft 32 and is detachably connected to the anti-disengagement end 23. The proximal section 321 of the shaft 32 is metal tubing made of layers of winded and threaded metal wires that can transmit torque. As shown in FIG. 8g, the shaft 32 is pushed to drive the anchoring needle 2 out of the distal end of the inner layer tube 311. At this moment, the distal end 21 of the anchoring needle penetrates the anchoring region 13, goes through the cardiac valve prosthesis 1 and pierces the autogenous tissue 6. After the anchoring needle 2 is pushed out of the delivery tube 31, the distal section 22 of the anchoring needle 2 restores its preset shape. As shown in FIGS. 8h-8i, through controlling the delivery system, the inner layer tube 311 is retracted, and the detachable connection between the delivery tube 31 and the cardiac valve prosthesis 1 is released. As shown in FIGS. 8j-8k, the operating member of the delivery system 4 is operated to force the shaft 32 to twist, thereby detaching the detachable connection between the anti-disengagement end 23 and the distal end 322 of the shaft, and releasing the anti-disengagement end 23, which makes the cardiac valve prosthesis 1 firmly fixed on the mitral valve annulus 10. The releasing device and the delivery system are further retracted, and the implanting process is completed.

As shown in FIG. 8l, the cardiac valve prosthesis 1 is firmly fixed on the mitral valve annulus 10 by three anchoring needles 2 finally. This embodiment can solve the problems in the traditional suture-fixed annuloplasty, which needs to make eleven to thirteen stitches and has long operating time.

The Sixth Embodiment

As shown in FIGS. 9a-9b, the implant with anchoring device for heart valve disease of the present invention comprises a cardiac valve prosthesis 1, two sets of anchoring needles 2, two sets of anchoring needle releasing devices 3, a delivery system 4, and two sets of supporting devices 8.

Figure 9C:
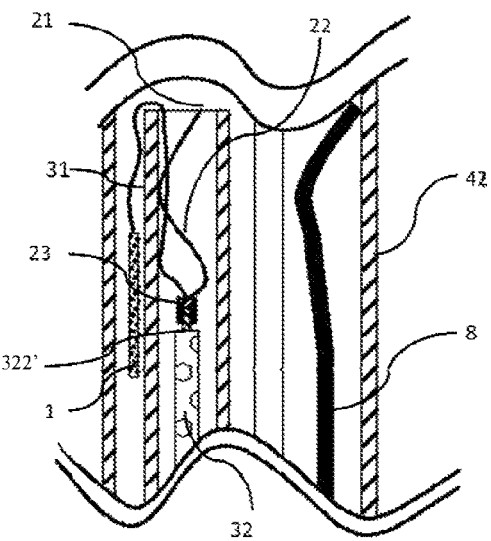

In some embodiments, as shown in FIG. 9a, the cardiac valve prosthesis 1, which is a prosthesis for repairing mitral valve or tricuspid valve, is applicable to the mitral valve or tricuspid valve repair surgery through the cardiac apex approach. The cardiac valve prosthesis 1 comprises a frame 11 and a leaflet 12. The frame 11 is by NI-TI shape memory alloy wires through winding and pre-heat-shaping process. The leaflet 12 is made of polymer membrane and is fixed on the frame 11. The leaflet 12 is provided with a frame construction, which is formed by NI-TI shape memory alloy wires through pre-heat-shaping process and is configured to protect the leaflet 12 from crinkling and turning over. The leaflet 12 moves along with the native heart valve, so as to prevent regurgitation. The nickel-titanium alloy wires of the frame 11 are clamped and welded with the anti-disengagement end 23 of the anchoring needle 2. The anti-disengagement end 23 is made of stainless steel bar with an external diameter of 0.95 mm, and is hollow and processed to have internal threads. As shown in FIG. 9c, the delivery tube 31 is made of a stainless steel tube with an internal diameter of 1.0 mm. The distal section of the delivery tube 31 has slits, which enable the distal section of the delivery tube 31 to bend wholly or partially. The length d from the most distal end of the delivery tube 31 to the most proximal end of the bent section of delivery tube 31 is larger than ⅙ of the circumference of the circle formed by the minimum radius of the native heart valve tissue annulus of a patient. The most distal end of the delivery tube 31 is provided with a rigid section, and the length of the rigid section is equal to the full length of the anchoring needle 2. The most distal end of the anchoring needle 2 is sharp, and the distal section 22 of the anchoring needle is pre-formed to be a structure having multiple arc segments with different radius. The distal section of the shaft 32 is provided with a metal head 322' with external screw threads, which are detachably connected to internal threads of the anti-disengagement end 23 of the anchoring needle 2, thereby realizing the detachable connection between the shaft 32 of the anchoring needle releasing device 3 and the cardiac valve prosthesis 1. The proximal section of the shaft 32 is metal tubing made of layers of winded and threaded metal wires that can transmit torque. In another embodiment (not shown), the anti-disengagement end 23 is made of stainless steel tube with an external diameter of 0.95 mm. Sufficient friction forces are generated between the pre-formed structure of the anchoring needle 2, the external diameter of anti-disengagement end 23 and the internal diameter of the delivery tube 31 due to the limitations of the dimensions and the pre-formed structure, thereby enabling the anchoring needle 2 and the delivery tube 31 to be fixed to each other. Additionally, under the push force from the shaft 32, the anchoring needle 2 can move towards the distal end of the delivery tube 31, thereby realizing the detachable connection between the anchoring needle 2 and the delivery tube 31. As the anchoring needle 2 is fixed on the cardiac valve prosthesis 1, the delivery tube 31 is detachably connected to the cardiac valve prosthesis 1 through the anchoring needle 2.

Figure 9D:
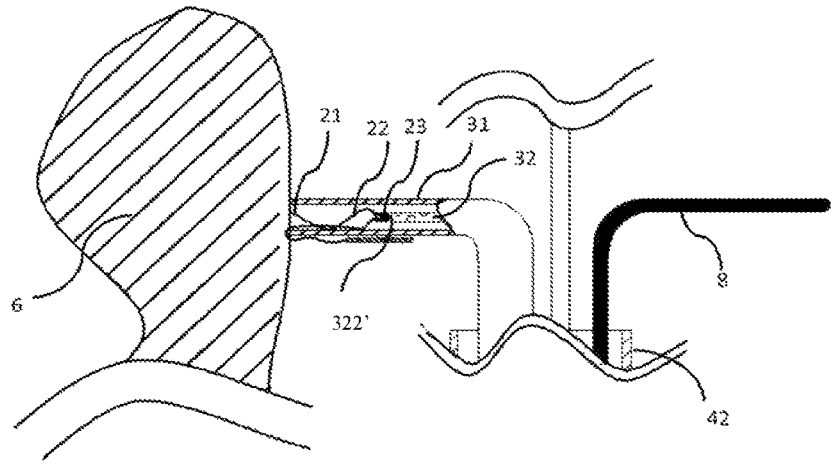
Figure 9E:
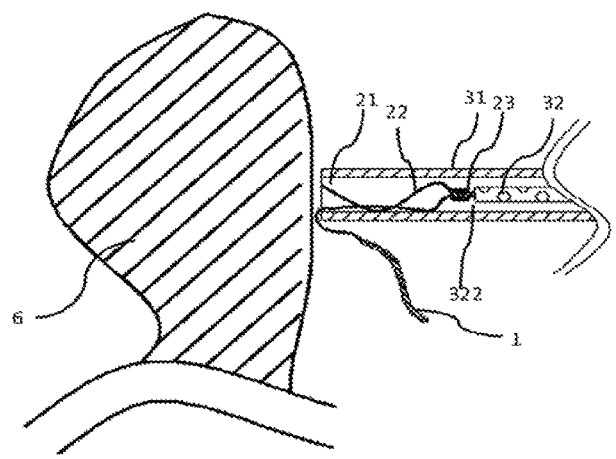
Figure 9F:
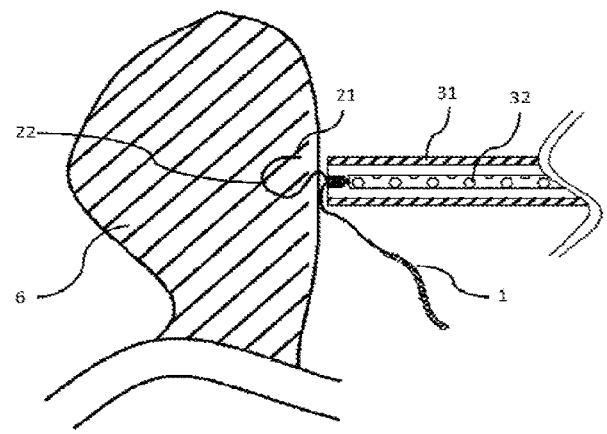
Figure 9G:
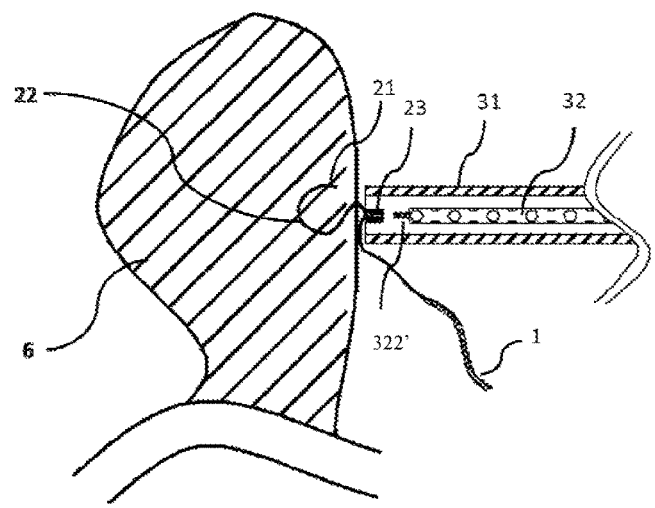
Figure 9H:
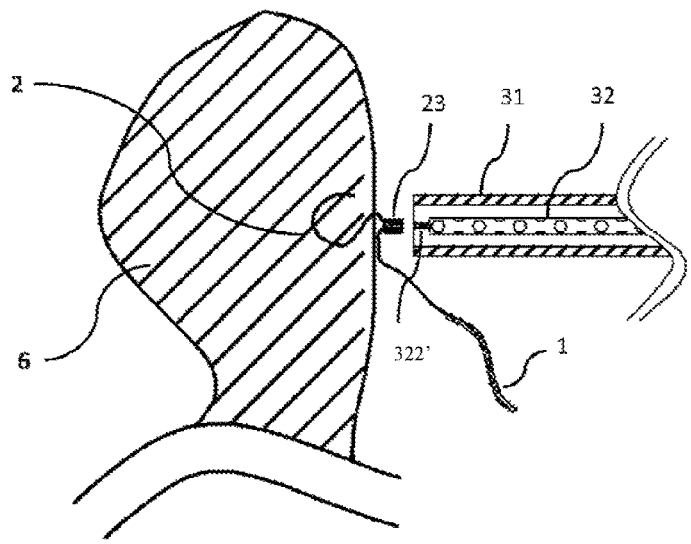

The operating method of the sixth embodiment differs from those of the embodiments described above in that: as shown in FIGS. 9c-9h, the outer sheath tube 42 is retracted, and the cardiac valve prosthesis 1 and the anchoring needle releasing device 3 are released; the delivery tube 31 bends to the state as shown in FIG. 9d. As shown in FIG. 9f, the operating member of the delivery system is operated to push the shaft 32, so that the anchoring needle 2 is pushed out of the delivery tube 31. The distal end 21 of the anchoring needle 2 pierces the autogenous tissue 6, and the distal section 22 of the anchoring needle restores to its preset arc shape, and the cardiac valve prosthesis 1 is fixed on the autogenous tissue 6. As shown in FIG. 9a, at this moment, the operating member of the delivery system is operated to force the shaft 32 to twist, thereby detaching the detachable connection between the anti-disengagement end 23 and the distal end 322 of the shaft, and releasing the anti-disengagement end 23, and detaching the detachable connection between the anchoring needle releasing device 3 and the cardiac valve prosthesis 1. As shown in FIG. 9h, the releasing device and the convey system are further retracted, and the implanting process is completed.

Finally, it should be noted that the above mentioned only illustrate preferred embodiments of the present invention, but not to limit the scope of the invention, and any amendments, equivalent replacements, improvements and so on made within the spirits and principles of the present invention all should be included in the protection scope of the present invention.

We claim:

1. An implant with anchoring device for heart valve disease, comprising a cardiac valve prosthesis, at least two sets of anchoring needles, and at least two sets of anchoring needle releasing devices; wherein, a most distal end of each anchoring needle is sharp; a distal section of each anchoring needle has a preset shape; a proximal end of each anchoring needle is provided with an anti-disengagement end; each anchoring needle releasing device comprises a delivery tube and a shaft; the delivery tube is detachably connected to the cardiac valve prosthesis through a connecting wire;

the delivery tube comprises at least two layers of tubes; one of the layers of tubes is disposed inside another of the layers of tubes; one end of the connecting wire is fixed at a distal section of any of the layers of tubes; another end of the connecting wire goes through the cardiac valve prosthesis and is winded back and clamped between distal sections of adjacent two of the layers of tubes; an operating member of the delivery tube is fixedly connected to a proximal end of the delivery tube; the at least two layers of tube can be moved to detach a detachable connection between the delivery tube and the cardiac valve prosthesis by controlling the operating member of the delivery tube; the implant with anchoring device for heart valve disease further comprises a delivery system; the delivery system comprises a tip, an outer sheath tube, a sheath core, and the operating member; the sheath core is arranged inside the outer sheath tube; a distal end of the sheath core is fixedly connected to the tip; the proximal end of the sheath core is fixedly connected to the operating member; the cardiac valve prosthesis and the anchoring needle releasing device are arranged between the outer sheath tube and the sheath core; a proximal end of the delivery tube is fixedly connected to the operating member; a detachable connection between the delivery tube and the cardiac valve prosthesis can be detached by operating the operating member;

a distal section of each anchoring needle releasing device is in a preset shape, which is configured to ensure that a distal section of the delivery tube to bend wholly or partially, and to enable a distal end of the delivery tube to press tightly against the cardiac valve prosthesis or press tightly against an anticipated position where the cardiac valve prosthesis to be fixed before each the anchoring needle is moved; a most distal end of the delivery tube has a rigid section; a bendable part of the delivery tube is a bent section; a length d from the most distal end of the delivery tube to a most proximal end of the bent section is larger than or equal to ⅙ of a circumference of a circle formed by a minimum radius of a native heart valve annulus of a patient; each anchoring needle is pre-placed inside the distal section of the delivery tube in a stretched state; the shaft is arranged inside the delivery tube; each anchoring needle is disposed beside a distal end of the shaft; the shaft can be pushed to force the anchoring needles to move toward the distal end of the delivery tube; the distal section of each anchoring needle restores to the preset shape after each anchoring needle is pushed out of the delivery tube, and the cardiac valve prosthesis is fixed to the anticipated position.

2. The implant with anchoring device for heart valve disease according to claim 1, wherein, a length of the rigid section of the delivery tube is greater than or equals to one tenth of a full length of each anchoring needle.

3. The implant with anchoring device for heart valve disease according to claim 1, wherein, the distal section of the delivery tube is pre-shaped to enable the distal section of the shaft to bend along with the pre-shaped distal section of the delivery tube; or the distal section of the shaft is pre-shaped to enable the bendable part of the delivery tube to bend along with the pre-shaped distal section of the shaft; or both the distal section of the delivery tube and the distal section of the shaft are pre-shaped to enable the distal section of the delivery tube and the distal section of the shaft to bend together.

4. The implant with anchoring device for heart valve disease according to claim 1, wherein, said implant with anchoring device for heart valve disease further comprises a supporting device and an operating member for the supporting device; the operating member for the supporting device is fixedly connected to a proximal end of the supporting device; a distal section of the supporting device is bendable, which makes the distal section of the supporting device press against the autogenous tissue when the supporting device is released.

5. The implant with anchoring device for heart valve disease according to claim 1, wherein, said implant with anchoring device for heart valve disease further comprises a supporting device and a delivery system; the delivery system comprises a tip, an outer sheath tube, a sheath core, and an operating member; the sheath core is arranged inside the outer sheath tube; a distal end of the sheath core is fixedly connected to the tip; a proximal end of the sheath core is fixedly connected to the operating member; the cardiac valve prosthesis, the anchoring needle releasing device, and the supporting device are arranged between the outer sheath tube and the sheath core; a proximal end of the supporting device is fixedly connected to the operating member of the delivery system; and when the anchoring needle releasing device is released, the supporting device exerts a supporting force on the anchoring needle releasing device.

6. The implant with anchoring device for heart valve disease according to claim 5, wherein, the supporting device is made of stainless steel tubes; the proximal end of the supporting device is fixedly connected to the operating member of the delivery system; the distal section of the supporting device has slits, which enables the distal section of the supporting device to bend; the distal section of the supporting device is movably connected to a rigid supporting rod; and a distal end of the supporting rod is movably connected to the tip.

7. The implant with anchoring device for heart valve disease according to claim 1, wherein, a distal section of the delivery tube is fixedly connected to a controlling wire to make it bent; a proximal end of the controlling wire is fixedly connected to an operating member for bend adjusting.

8. The implant with anchoring device for heart valve disease according to claim 1, wherein, the anti-disengagement end of each anchoring needle is formed by further extending and winding the proximal end of each anchoring needle.

9. The implant with anchoring device for heart valve disease according to claim 8, wherein, the shaft is detachably connected to the anti-disengagement end of each anchoring needle.

10. The implant with anchoring device for heart valve disease according to claim 1, wherein, each anchoring needle is fixedly connected on the cardiac valve prosthesis; and a detachable connection between each anchoring needle releasing devices and the cardiac valve prosthesis is realized by a detachable connection between each anchoring needle and each anchoring needle releasing devices.

11. The implant with anchoring device for heart valve disease according to claim 1, wherein, the shaft is detachably connected to the anti-disengagement end of each anchoring needle.

12. The implant with anchoring device for heart valve disease according to claim 1, wherein, said implant with anchoring device for heart valve disease further comprises a supporting device and a delivery system; the delivery system comprises a tip, an outer sheath tube, a sheath core, and an operating member; the sheath core is arranged inside the outer sheath tube; a distal end of the sheath core is fixedly connected to the tip; a proximal end of the sheath core is fixedly connected to the operating member; the cardiac valve prosthesis, each anchoring needle releasing device, and the supporting device are arranged between the outer sheath tube and the sheath core; the distal section of the supporting device is fixedly connected to the tip of the delivery system; and when each anchoring needle releasing device is released, the supporting device exerts a supporting force on each anchoring needle releasing device.

13. The implant with anchoring device for heart valve disease according to claim 1, wherein, said implant with anchoring device for heart valve disease further comprises a supporting device and a delivery system; the delivery system comprises a tip, an outer sheath tube, a sheath core, and an operating member; the sheath core is arranged inside the outer sheath tube; a distal end of the sheath core is fixedly connected to the tip; a proximal end of the sheath core is fixedly connected to the operating member; the cardiac valve prosthesis, each anchoring needle releasing device, and the supporting device are arranged between the outer sheath tube and the sheath core; the proximal end of the supporting device is fixedly connected to the operating member of the delivery system, and the distal section of the supporting device is fixedly connected to the tip of the delivery system; and when each anchoring needle releasing device is released, the supporting device exerts a supporting force on each anchoring needle releasing device.

\* \* \* \* \*